United States Patent
Reed et al.

(10) Patent No.: US 10,451,636 B2
(45) Date of Patent: Oct. 22, 2019

(54) PROTEIN BIOMARKERS FOR IMMUNE ASSESSMENT AND PREDICTION OF TRANSPLANT REJECTION

(71) Applicant: THE REGENTS OF THE UNIVERSITY OF CALIFORNIA, Oakland, CA (US)

(72) Inventors: Elaine F. Reed, Malibu, CA (US); Hans Albin Gritsch, Los Angeles, CA (US); Jeffrey Lorne Veale, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 71 days.

(21) Appl. No.: 15/302,463

(22) PCT Filed: Apr. 9, 2015

(86) PCT No.: PCT/US2015/025164
§ 371 (c)(1),
(2) Date: Oct. 6, 2016

(87) PCT Pub. No.: WO2015/157546
PCT Pub. Date: Oct. 15, 2015

(65) Prior Publication Data
US 2017/0030928 A1 Feb. 2, 2017

Related U.S. Application Data

(60) Provisional application No. 61/977,567, filed on Apr. 9, 2014.

(51) Int. Cl.
| | | |
|---|---|---|
| *C07K 14/75* | (2006.01) |
| *C07K 14/81* | (2006.01) |
| *C07K 16/18* | (2006.01) |
| *G01N 33/53* | (2006.01) |
| *G01N 33/543* | (2006.01) |
| *G01N 33/544* | (2006.01) |
| *G01N 33/551* | (2006.01) |
| *G01N 33/58* | (2006.01) |
| *G01N 33/68* | (2006.01) |
| *C07K 14/775* | (2006.01) |

(Continued)

(52) U.S. Cl.
CPC ....... *G01N 33/6893* (2013.01); *C07K 14/472* (2013.01); *C07K 14/775* (2013.01); *C07K 14/81* (2013.01); *C07K 14/8121* (2013.01); *C07K 16/18* (2013.01); *G01N 33/53* (2013.01); *G01N 33/543* (2013.01); *G01N 33/544* (2013.01); *G01N 33/551* (2013.01); *G01N 33/58* (2013.01); *G01N 33/68* (2013.01); *G01N 33/6854* (2013.01); *G01N 2030/8813* (2013.01); *G01N 2333/4716* (2013.01); *G01N 2333/775* (2013.01); *G01N 2333/81* (2013.01); *G01N 2333/811* (2013.01); *G01N 2800/245* (2013.01)

(58) Field of Classification Search
CPC ........ C12Q 2563/143; C12Q 2565/633; C12Q 1/6825; C12Q 1/686; C12Q 2565/113; C12Q 2525/205; C12Q 1/6827; C12Q 1/6895; C12Q 2537/101; C12Q 2537/143; C12Q 2563/149; C12Q 2600/158; C12Q 2600/156; C12Q 1/6883; C12Q 1/6816; C12Q 2537/125; C12Q 2563/155; C12Q 1/6811; C12Q 1/6886; C12Q 1/6851; C12Q 1/689; C12Q 1/701; C12Q 1/70; C12Q 2600/112; C12Q 1/25; C12Q 1/37; C12Q 1/48; C12Q 2600/142; C12Q 1/26; C12Q 2600/106; C12Q 2600/178; A61K 2039/505; A61K 39/395; A61K 39/39533; A61K 39/3955; C07K 2317/76; C07K 14/775; C07K 16/18; C07K 16/44
See application file for complete search history.

(56) References Cited

U.S. PATENT DOCUMENTS

| | | |
|---|---|---|
| 7,026,121 B1 | 4/2006 | Wohlgemuth et al. |
| 7,192,716 B2 | 3/2007 | Rose et al. |
| 7,235,358 B2 | 6/2007 | Wohlgemuth et al. |

(Continued)

FOREIGN PATENT DOCUMENTS

| | | |
|---|---|---|
| EP | 2281203 B1 | 2/2012 |
| EP | 2350669 B1 | 8/2013 |

(Continued)

OTHER PUBLICATIONS

Abe et al. Anti-apolipoprotein A-I autoantibody: characterization of monoclonal antibodies from patients with systemic lupus erythematosus. J Rheumatol 28: 990-995, 2001.*

(Continued)

*Primary Examiner* — Bridget E Bunner
(74) *Attorney, Agent, or Firm* — Karen S. Canady; canady + lortz LLP

(57) ABSTRACT

The invention provides a method for screening for and detection of solid organ graft rejection in a subject that comprises assaying a patient sample of plasma, serum or blood from the subject for a protein marker identified herein. An elevated or reduced amount of marker present in the patient sample compared to a control sample is indicative of rejection, and identifies subjects in need of biopsy or modified treatment. The method can be used to screen for patients in danger of transplant rejection without having to undergo more costly, risky and invasive biopsy procedures.

19 Claims, 8 Drawing Sheets
Specification includes a Sequence Listing.

(51) Int. Cl.
*C07K 14/47* (2006.01)
*G01N 30/88* (2006.01)

(56) References Cited

U.S. PATENT DOCUMENTS

| | | | |
|---|---|---|---|
| 7,645,575 | B2 | 1/2010 | Wohlgemuth et al. |
| 7,666,596 | B2 | 2/2010 | Halloran |
| 7,691,569 | B2 | 4/2010 | Wohlgemuth et al. |
| 8,003,333 | B2 | 8/2011 | Charlton |
| 8,021,895 | B2 | 9/2011 | Kienle et al. |
| 8,039,227 | B2 | 10/2011 | Klein et al. |
| 8,592,170 | B2 | 11/2013 | Barasch et al. |
| 2003/0104371 | A1 | 6/2003 | Strom et al. |
| 2006/0088836 | A1 | 4/2006 | Wohlgemuth et al. |
| 2007/0037166 | A1 | 2/2007 | Wohlgemuth et al. |
| 2007/0202085 | A1 | 8/2007 | Hu et al. |
| 2008/0038746 | A1 | 2/2008 | Rosenberg et al. |
| 2009/0022730 | A1 | 1/2009 | Raulf et al. |
| 2009/0053195 | A1 | 2/2009 | Raulf et al. |
| 2009/0304705 | A1 | 12/2009 | Grass |
| 2012/0046181 | A1 | 2/2012 | Chu Nantes et al. |
| 2013/0052665 | A1* | 2/2013 | Ling ............... G01N 33/6893 435/7.92 |
| 2013/0230871 | A1 | 9/2013 | Anderberg et al. |
| 2013/0323751 | A1 | 12/2013 | Singbartl et al. |
| 2014/0038203 | A1 | 2/2014 | Arthur et al. |

FOREIGN PATENT DOCUMENTS

| | | |
|---|---|---|
| WO | WO2001081916 A3 | 8/2003 |
| WO | WO2004005934 A2 | 1/2004 |
| WO | WO2004030521 A2 | 4/2004 |
| WO | WO2004042346 A3 | 5/2004 |
| WO | WO2007104537 A2 | 9/2007 |
| WO | WO2007121922 A3 | 12/2007 |
| WO | WO2007138011 A1 | 12/2007 |
| WO | WO2008084331 A2 | 7/2008 |
| WO | WO2008027428 A3 | 9/2008 |
| WO | WO2009045104 A1 | 4/2009 |
| WO | WO2009101083 A1 | 8/2009 |
| WO | WO2011017685 A1 | 2/2011 |
| WO | WO2012146778 A2 | 11/2012 |

OTHER PUBLICATIONS

Ahn et al. Serum biomarker panels for the diagnosis of gastric adenocarcinoma. Brit J Cancer 106: 733-739, 2012.*
AssayMax Human alpha-2-macroglobulin ELISA kit manual, catalog #EM1115-1, Oct. 17, 2010; 6 total pages.*
AssayMax Huamn apolipoprotein A-I ELISA kit manual, catalog #EA5301-1, Feb. 14, 2013; 12 total pages.*
Dreyfus et al. Successful rituximab B lymphocyte depletion therapy for angioedema due to acquired C1 inhibitor protein deficiency: association with reduced C1 inhibitor protein autoantibody titers. IMAJ 16: 315-316, 2014.*
Ho et al. Novel biomarkers predict liver fibrosis in hepatitis C patients: alpha 2 macroglobulin, vitamin D binding protein and apolipoprotein A1. J Biomed Sci 17: 58, 2010 (8 total pages).*
Imai et al. Natural autoantibody against apolipoprotein A-I. Detection and characterization of the monoclonal antibody established from normal unimmunized BALB/c mice. J Immunol 153: 2290-2301, 1994.*
Jespersen et al. The reference range for complexed alpha2-macroglobulin human plasma: development of a new enzyme linked immunosorbent assay (ELISA) for quantitation of complexed alpha2-macroglobulin. Scand J Clin Lab Invest 53: 639-648, 1993.*
Morita-Hoshi, Y, et al., Identification of molecular markers for pre-engraftment immune reactions after cord blood transplantation by SELDI-TOF MS. Bone Marrow Transplantation (2010) 45, 1594-1601; doi:10.1038/bmt.2010.18; published online Mar. 15m 2010.
Extended European Search Report dated Sep. 8, 2017 for corresponding EP Application 15777119.7.
Abou-Ragheb,HH, et al., Plasma levels and mode of excretion of the anaphylatoxins C3a and C4a in renal disease. J Clin Lab Immunol. Jul. 1991;35(3):113-9. Abstract only.
Bao, Yang et al., Proteomic profiling of heterotopic heart-transplanted rats using surface-enhanced laser desorption/ionization time-of-flight mass spectrometry: potential biomarkers and drug targets. J Int Med Res. Jun. 2013;41(3):628-35. doi: 10.1177/0300060513476997. Epub Apr. 18, 2013.
Fukuda, Y., et al., Examination of Serum Amyloid a Protein in Kidney Transplant Patients—Comparison of Serum Amyloid a and C-Reactive Protein for Monitoring the Occurrence of Renal-allograft-related Complications. Hiroshima Journal of Medical Sciences 47(2):63-7, Jul. 1998.
Hartmann, A., et al., Serum amyloid a protein is a clinically useful indicator of acute renal allograft rejection. Nephrol Dial Transplant. Jan. 1997;12(1):161-6.
Jia, X., et al., Detection of urinary biomarkers for early diagnosis of acute renal allograft rejection by proteomic analysis. Proteomics. vol. 3, Issue 6. Jun. 2009. pp. 694-704.
Lin, David Chia-Hsiang, Thesis: Biomarkers of Acute and Chronic Human Heart Allograft Rejection.The University of British Columbia, Vancouver. 2012.
Massoud, Omar, et al., Noninvasive diagnosis of acute cellular rejection in liver transplant recipients: a proteomic signature validated by enzyme-linked immunosorbent assay. Liver Transpl. Jun. 2011;17(6):723-32. doi: 10.1002/lt.22266.
Maury, CP., et al, Acute phase proteins and liver allograft rejection. Liver. Apr. 1988;8(2):75-9.
O'Riordan, E., et al, Characterization of Urinary Peptide Biomarkers of Acute Rejection in Renal Allografts. American Journal of Transplantation 2007; 7: 930-940.
Pfeifer, P., et al., Plasma C3a and C4a levels in liver transplant recipients: a longitudinal study. Immunopharmacology. Feb. 2000;46(2):163-74.
Roedder, S., et al., Biomarkers in solid organ transplantation: establishing personalized transplantation medicine. Roedder et al. Genome Medicine 2011, 3:37.
Rowe, I.F., et al., Measurement of serum C-reactive protein concentration after renal transplantation. Nephrol Dial Transplant. 1987;2(1):39-41.
Schaub, S. et al., Proteomics and Renal Transplantation: Searching for Novel Biomarkers and Therapeutic Targets, in Proteomics in Nephrology; Towards Clinical Applications, edited by V. Thongboonkerd, Contributions in Nephrology vol. 160, Karger, 2008, p. 65-75; doi:10.1159/000125934. http://www.karger.com/Article/Abstract/125934.
Ziegler, M.E., et al., Apolipoprotein A1 and C-terminal fragment of alpha-1 antichymotrypsin are candidate plasma Biomarkers associated with acute renal allograft rejection, Transplantation (Aug. 27, 2011) 92(4):388-396; doi: 10.1097/TP.0b013e318225db6a. http://www.ncbi.nlm.nih.gov/pmc/articles/PMC3878300/.
International Search Report and Written Opinion dated Jun. 29, 2016 for corresponding application PCT/US2015/025164 filed, Apr. 9, 2016.

* cited by examiner

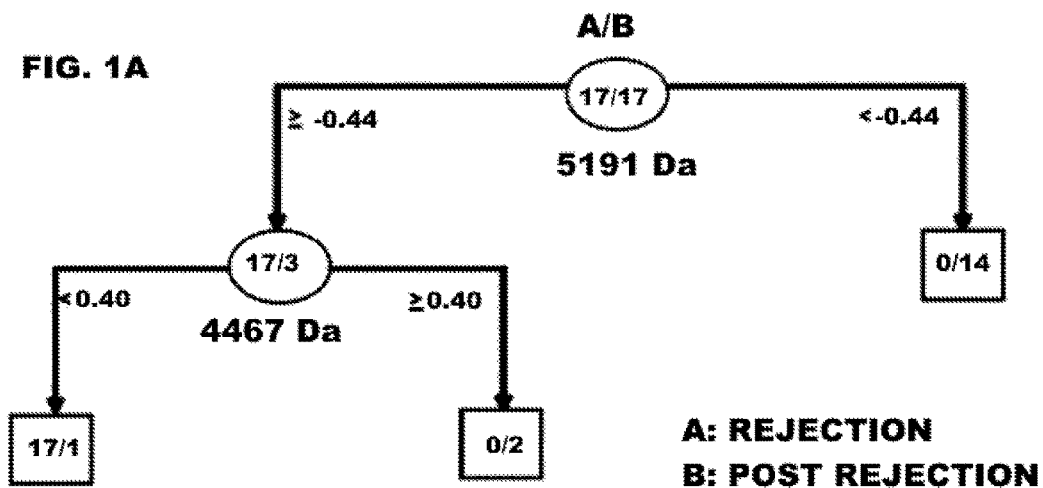
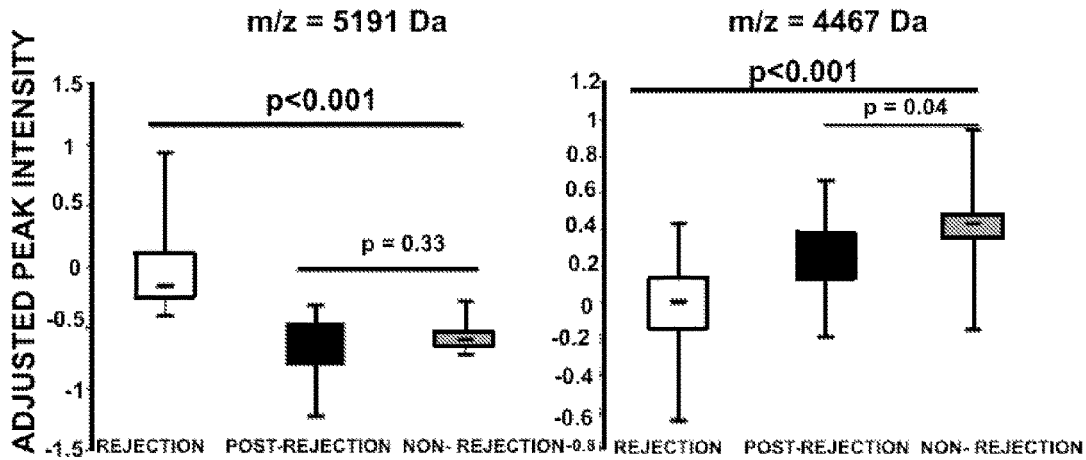

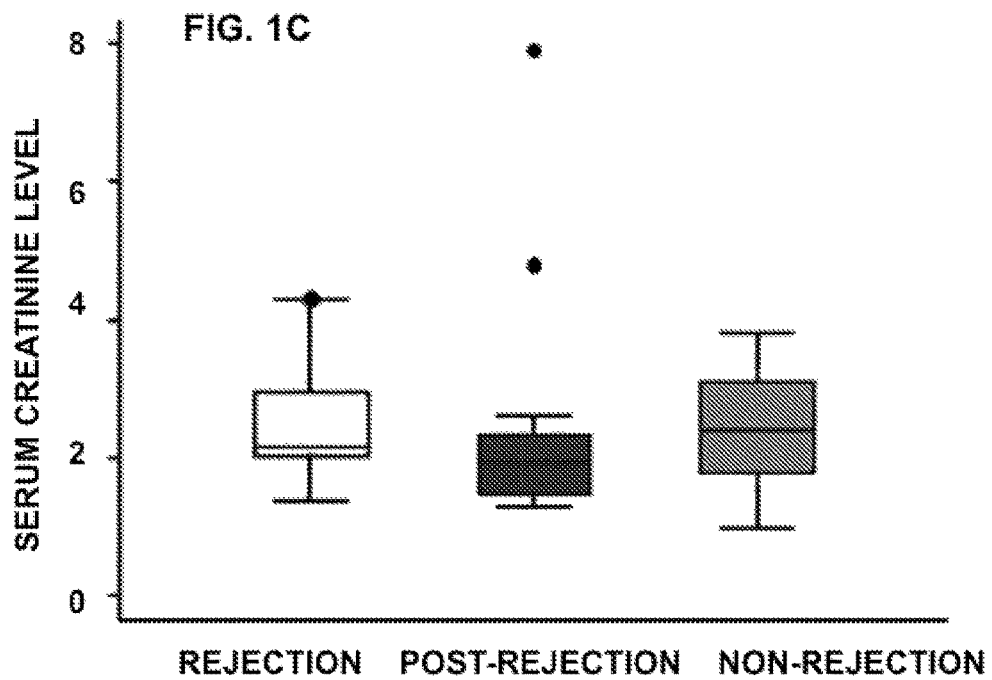
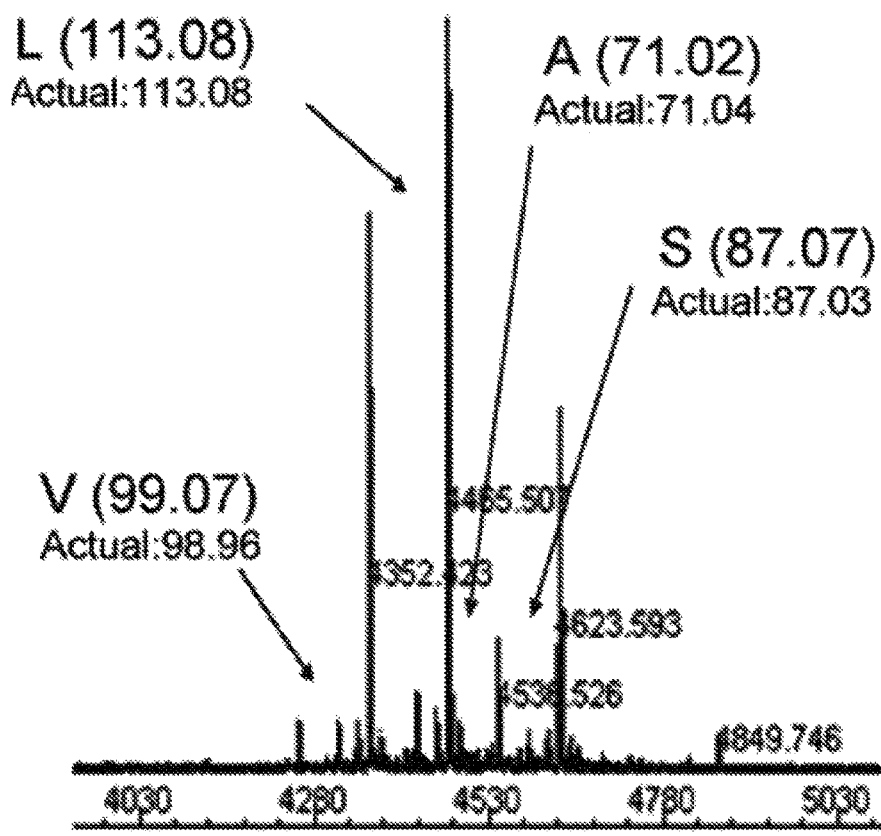

PROTEIN BIOMARKERS FOR IMMUNE ASSESSMENT AND PREDICTION OF TRANSPLANT REJECTION

This application claims the benefit of U.S. provisional patent application No. 61/977,567, filed Apr. 9, 2014, the entire contents of which are incorporated herein by reference.

TECHNICAL FIELD OF THE INVENTION

The present invention relates generally to detection, prediction, and monitoring of transplant rejection, including renal allograft rejection. The invention more specifically pertains to use of protein markers that can be detected in serum for early detection of allograft rejection.

BACKGROUND OF THE INVENTION

A transplant to replace damaged tissues with healthy ones from either living or decreased individuals of the same species is called an allograft. Tissues and cells from another individual are usually recognized as foreign by the mammalian immune system. This stimulates a response of the host defenses to reject the foreign tissue. The immune system can occasionally recognize very small differences in molecular structure and develop an alloimmune response. Some cell types are very similar among individuals such as blood cells. It is possible to administer blood products such red blood cells, and plasma without an immune response if the blood type is compatible. Virtually all mammalian cells, except red blood cells, express major histocompatibility molecules on their cell surface. These molecules are a critical mechanism by which the immune system can distinguish self from foreign cells.

Organ transplantation is the definitive therapy for many forms of end-stage disease of the kidney, liver, heart, lung, pancreas and intestine. Transplantation of specialized cells such as islets of Langerhans and nerve cells are becoming more common, as well as complex tissue transplantation such as a limb or face. However, the long-term success of these procedures is limited by the immune response. Unless the donor is an identical twin, most recipients must take immunosuppressive medications. Current immunosuppressive therapies are not capable of preventing rejection in all cases, and have multiple significant side effects. These drugs may lead to life threatening infection, cardiovascular disease, diabetes, and cancer.

A number of methods are currently used to monitor the function of transplanted organs and tissue: serum creatinine for kidney, serum transaminases for liver, ejection fraction for heart, oxygen saturation for lung, and serum glucose for pancreas transplant. Unfortunately, these tests have poor sensitivity or specificity for rejection. In many cases the definitive test for organ rejection is an invasive and expensive biopsy.

The histologic patterns of rejection are different for each organ and distinct patterns of tissue injury can be identified for "cellular" versus "humoral" rejection. This distinction is important since the best treatment for "cellular" rejection may be administration of immunosuppressive medications targeted to prevent further proliferation of T lymphocytes, while "humoral" rejection is treated by medications that suppress B lymphocytes and clear the plasma of the antibodies which recognize the graft as foreign. In general, a mild cellular rejection can frequently be reversed and may not cause long-term injury. Humoral rejection is more difficult to reverse and has a higher risk of leading to poor graft function. In many cases of transplant rejection there are components of both a cellular and humoral immune response combined. The gold standard for classification of transplant rejection is allograft biopsy.

Despite significant improvements in one-year allograft function with current immunosuppressive strategies, there has been less progress in the long term maintenance of graft function. It is hypothesized that both immunologic and non-immunologic factors such as drug toxicity or hypertension contribute to this disease. Chronic transplant dysfunction is a phenomenon in solid organ transplants with a gradual deterioration of function accompanied by characteristic histological features on graft biopsy. In kidney transplantation, this is known as chronic rejection, chronic allograft nephropathy (CAN), or interstitial fibrosis with tubular atrophy (IFTA). In heart transplantation there is accelerated atherosclerosis and in liver transplantation the bile ducts atrophy. Chronic transplant injury is characterized by fibrosis of the internal blood vessels of the transplant and may be related to sub-clinical AMR. Detecting this problem at an early stage is difficult even with protocol biopsy.

Current diagnostic methods of renal allograft rejection are neither sensitive nor specific. Needle biopsies are invasive and associated with patient morbidity. Thus, it is desirable to develop noninvasive tests to predict and diagnose rejection.

SUMMARY OF THE INVENTION

The invention provides a set of protein markers and methods of using these markers for assessment of a patient's immune status and for predicting rejection of an organ transplant. The markers include complement C4 anaphylatoxin (C4A), Apolipoprotein A1 (ApoA1), α-1 anti-chymotrypsin C terminal fragment (AACT), C1 protease inhibitor (C-inh), Serum Amyloid A (SAA), C-reactive Protein (CRP), Apolipoprotein E (ApoE), alpha-1-antitrypsin (A1AT), Post-translational modified ApoA1, Inter-alpha-trypsin inhibitor heavy chain H4 (ITIH4), and Alpha-2-macroglobulin (A2M), as well fragments of these proteins (see Tables 1 and 4, and SEQ ID NOs: 1-18).

The invention provides a method for detecting susceptibility in a patient to solid organ graft rejection, which can be achieved with a high degree of sensitivity and specificity. In one embodiment, the method detects rejection with at least 90% sensitivity and at least 90% specificity. In one embodiment, the method comprises the steps of: (a) measuring the amount of a 5 kiloDalton (kDa) fragment of complement C4 anaphylatoxin (C4A) in a sample obtained from the patient; (b) comparing the amount of the 5 kDa fragment of C4A in the patient sample with the amount in a control sample; and (c) detecting susceptibility to graft rejection when the comparing shows an increase in the 5 kDa fragment of C4A in the patient sample relative to the control sample. In another embodiment, the method comprises the steps of: (a) contacting a sample obtained from the patient with a reagent that specifically binds a 5 kiloDalton (kDa) fragment of complement C4 anaphylatoxin (C4A); (b) measuring the amount of specific binding between the reagent and the patient sample; (c) comparing the amount of specific binding in (b) with the amount of specific binding of reagent to a control sample; and (d) detecting susceptibility to graft rejection when the comparing in (c) shows an increase in specific binding to the 5 kDa fragment of C4A in the patient sample relative to the control sample. In one embodiment, the contacting further comprises contacting the patient sample with a reagent that binds Apolipoprotein A1 (ApoA1) and/or α-1 anti-chymotrypsin C terminal fragment (AACT), and the detecting further comprises detecting susceptibility to graft rejection when the comparing shows a decrease in the amount of ApoA1 and/or AACT in the patient sample relative to the control sample. In one embodiment, the contacting and comparing of (b) and (c) comprise contacting the patient sample with reagents that bind ApoA1 and AACT.

In another embodiment, the invention provides a method for detecting susceptibility in a patient to solid organ graft rejection. In one embodiment, the method comprises the steps of: (a) contacting a sample obtained from the patient with a reagent that specifically binds a set of biomarkers comprising two or more markers listed in Table 1; (b) measuring the amount of specific binding between the reagents and the patient sample; (c) comparing the amount of specific binding in (b) with the amount of specific binding of the reagents to a control sample; and (d) detecting susceptibility to graft rejection when the comparing in (c) shows a significant increase or decrease in specific binding to the biomarkers in the patient sample relative to the control sample. In some embodiments, steps (a)-(c) are performed for 2, 3, 4, 5, 6, 7, 8, 9, 10, 12, 15, up to 19 of the markers listed in Table 1. In one embodiment, the set of markers consists of 8 or fewer markers listed in Table 1. In another embodiment, the set of markers consists of 6 or fewer markers listed in Table 1. In yet another embodiment, the set of markers consists of 4 or fewer markers listed in Table 1.

With respect to the following markers, susceptibility to graft rejection is detected when the specific binding of reagent to marker is increased in the patient sample relative to the control: C1 protease inhibitor (C1-inh), Serum Amyloid A (SAA), C-reactive Protein (CRP), Apolipoprotein E (ApoE), alpha-1-antitrypsin (A1AT), and/or specific binding of reagent to the following markers is decreased relative to control: AACT, ApoA1, Post-translational modified ApoA1, Inter-alpha-trypsin inhibitor heavy chain H4 (ITIH4), Alpha-2-macroglobulin (A2M). In a typical embodiment, the difference is a decrease or increase of at least 10% relative to the control.

In another embodiment, the invention provides a method for detecting susceptibility in a patient to solid organ graft rejection, the method comprising the steps of: (a) contacting a sample obtained from the patient with reagents that specifically bind a set of markers consisting of: a 5191 Dalton fragment of complement C4 anaphylatoxin (C4A), α-1 anti-chymotrypsin C terminal fragment (AACT), and Apo A1; and optionally further consisting of: complement C1 inhibitor, and/or a marker listed in Table 1; (b) measuring the amount of specific binding between the reagent and the sample; (c) comparing the amount of specific binding in (b) with a control sample; and (d) detecting susceptibility to graft rejection when the comparing in (c) shows an increase in the 5191 Dalton fragment of C4A or a decrease AACT and/or ApoA1 relative to the control sample.

In some embodiments, the measuring comprises an immunoassay. In other embodiments, the measuring comprises mass spectrometry. Representative examples of reagents include, but are not limited to, an antibody, a nucleic acid probe, or a synthetic probe. The probe or antibody may optionally be labeled with a detectable marker.

Examples of solid organ grafts include, but are not limited to, kidney, liver, heart, pancreas, lung, intestine and thymus. In one embodiment, the solid organ graft rejection is acute cellular renal allograft rejection. Other types of solid organ graft rejection include chronic rejection, such as chronic allograft nephropathy, or interstitial fibrosis with tubular atrophy.

The invention additionally provides a kit comprising antibodies that specifically bind the 5 kDa fragment of C4A, ApoA1, AACT, and, optionally, one or more additional markers listed in Table 1. In one embodiment, the kit comprises reagents that bind C4A (or a 5 kDa fragment thereof) and ApoA1 (or the fragment thereof at amino acids 148-183) and/or AACT (or the fragment thereof at amino acids 385-422), In one embodiment, the kit comprises reagents that specifically bind the 5191 Da fragment of AACT and ApoA1. In one embodiment, the kit further comprises a solid support onto which the antibodies are immobilized. Examples of a solid support include, but are not limited to, a microtiter plate, beads, a membrane or other support known to those skilled in the art. In one embodiment, the antibodies are immobilized via binding to antigen that is immobilized to the solid support. In one embodiment, the antibodies are immobilized via binding to a bead or particle such as luminex. In one embodiment, the kit further comprises a chromogenic substrate.

Additionally provided is a method for detecting susceptibility in a patient to solid organ graft rejection, the method comprising the steps of: (a) contacting a sample obtained from the patient with a reagent that specifically binds complement C4 anaphylatoxin (C4A); (b) measuring the amount of specific binding between the reagent and the sample; (c) comparing the amount of specific binding in (b) with a control sample; wherein a greater amount of binding in (b) relative to the control is indicative of susceptibility to solid organ graft rejection.

Another illustrative embodiment of the invention is a mass spectrometry assay to identify the peptide and/or protein profile in a patient that is associated with solid organ allograft rejection by detecting α-1 anti-chymotrypsin and/or Apo A1 and/or C4A and/or complement C1 inhibitor and/or one of the other 16 proteins in Table 1 in plasma or serum or other body fluid, the assay comprising the steps of: (a) measuring the specific amount of specific peptide by mass spectrometry in plasma, serum or other body fluid; (b) comparing the specific quantity of protein/peptide in (a) with a control sample; wherein a greater or lesser amount of specific peptide relative to the control is indicative of susceptibility to solid organ graft rejection.

Another illustrative embodiment of the invention is an ELISA kit to screen for a plasma molecular profile in a patient that is associated with acute cellular renal allograft rejection by detecting α-1 anti-chymotrypsin and/or Apo A1 and/or C4A and/or complement C1 inhibitor in plasma or serum, the kit comprising: (a) a microtiter plate coated with polyclonal or monoclonal antibodies specific to α-1 anti-chymotrypsin and/or Apo A1 and/or C4A and/or complement C1 inhibitor; (b) polyclonal or monoclonal antibody-alkaline phosphatase conjugates reactive with α-1 anti-chymotrypsin and/or Apo A1 and/or C4A and/or complement C1 inhibitor; (c) p-nitrophenyl-phosphate; and (d) α-1 anti-chymotrypsin and/or Apo A1 and/or C4A and/or complement C1 inhibitor as an antigen standard.

Also provided is a method for detecting susceptibility in a patient to acute cellular renal allograft rejection, the method comprising the steps of: (a) providing polyclonal or monoclonal antibodies against α-1 anti-chymotrypsin and/or Apo A1 and/or C4A and/or complement C1 inhibitor; (b) providing a microtiter plate coated with the antibodies; (c) adding the serum or plasma to the microtiter plate; (d) providing alkaline phosphatase-antibody conjugates reactive with α-1 anti-chymotrypsin and/or Apo A1 and/or C4A and/or complement C1 inhibitor to the microtiter plate; (e) providing p-nitrophenyl-phosphate to the microtiter plate; and (f) comparing the reaction which occurs as a result of steps (a) to (e) with a standard curve to determine the levels of α-1 anti-chymotrypsin and/or Apo A1 and/or C4A and/or complement C1 inhibitor compared to a normal individual.

Another illustrative embodiment of the invention is an ELISA kit to screen for a plasma molecular profile in a patient that is associated with acute cellular renal allograft rejection by detecting α-1 anti-chymotrypsin and/or Apo A1 and/or C4A and/or complement C1 inhibitor in plasma or serum, the kit comprising: (a) a microtiter plate coated with polyclonal or monoclonal antibodies specific to α-1 anti-chymotrypsin and/or Apo A1 and/or C4A and/or complement C1 inhibitor; (b) polyclonal or monoclonal antibody-alkaline phosphatase conjugates reactive with α-1 anti-chymotrypsin and/or Apo A1 and/or C4A and/or complement C1 inhibitor; (c) p-nitrophenyl-phosphate; and (d) α-1 anti-chymotrypsin and/or Apo A1 and/or C4A and/or complement C1 inhibitor as an antigen standard.

Another illustrative embodiment of the invention is a Luminex kit to screen in plasma, serum and\or biological fluid for a molecular profile in a patient that is associated with solid organ allograft rejection by detecting α-1 anti-chymotrypsin and/or Apo A1 and/or C4A and/or complement C1 inhibitor and/or proteins described in Table 1, the kit comprising: (a) a microbead array coated with polyclonal or monoclonal antibodies specific to α-1 anti-chymotrypsin and/or Apo A1 and/or C4A and/or complement C1 inhibitor and/or other proteins listed in Table 1; (b) polyclonal or monoclonal antibody fluorescent dye conjugates reactive with α-1 anti-chymotrypsin and/or Apo A1 and/or C4A and/or complement C1 inhibitor and/or other proteins listed in Table 1; (c) and α-1 anti-chymotrypsin and/or Apo A1 and/or C4A and/or complement C1 inhibitor or other protein in Table 1 as an antigen standard.

Embodiments of the invention provide assays and methods for the detection and/or quantitation in a sample of: AACT and/or Apo A1 and/or C4A and/or SAA and/or CRP and/or A2M and/or ApoE and/or ITIH4 and/or A1AT and/or C-inh and/or fragments of these polypeptides. Typical embodiments of the invention utilize ELISA-type assays of the type that are suitable for use with biological fluid samples such as blood, plasma, serum, or other bodily fluids of a mammal, particularly a human. Methodological embodiments include testing for the amounts of AACT and/or C4A and/or Apo A1 polypeptides, fragments of these markers, and/or a combination of the markers described herein in biological fluid samples. Certain embodiments examine together: α-1 antichymotrypsin, Apo A1, complement C1 inhibitor and the 5191 Da peptide of C4A in order to, for example, identify a plasma molecular profile in a patient that is associated with acute cellular renal allograft rejection. Certain embodiments examine 1 (e.g. the 5191 Da C4A peptide) or 2 (e.g. C4A peptide plus α-1 antichymotrypsin or Apo A1) or 3 (e.g. α-1 antichymotrypsin, Apo A1 and the 5191 Da C4A peptide) or all 4 of these biomarkers.

In certain embodiments of the invention, the 5191 Da C4A peptide is purified and this purified peptide is then injected into animals such as a rabbits to generate polyclonal antibodies specific to the 5191 Da peptide that can be used in ELISA tests and the like. Similarly, monoclonal antibody preparations to the protein may be prepared by injecting the purified 5191 Da peptide into mice, harvesting the spleen and lymph node cells, fusing these cells with mouse myeloma cells and using the resultant hybridoma cells to produce the monoclonal antibody.

One illustrative embodiment of the invention is a method for detecting α-1 anti-chymotrypsin and/or Apo A1 and/or the 5191 peptide disclosed herein and/or complement C1 inhibitor in plasma to screen for a plasma molecular profile in a patient that is associated with acute cellular renal allograft rejection comprising the steps of: (a) providing polyclonal or monoclonal antibodies against α-1 anti-chymotrypsin and/or Apo A1 and/or the 5191 peptide disclosed herein and/or complement C1 inhibitor; (b) providing a microtiter plate coated with the antibodies; (c) adding the serum or plasma to the microtiter plate; (d) providing alkaline phosphatase-antibody conjugates reactive with α-1 anti-chymotrypsin and/or Apo A1 and/or the 5191 peptide disclosed herein and/or complement C1 inhibitor to the microtiter plate; (e) providing p-nitrophenyl-phosphate to the microtiter plate; and (f) comparing the reaction which occurs as a result of steps (a) to (e) with a standard curve to determine the levels of α-1 anti-chymotrypsin and/or Apo A1 and/or the 5191 peptide disclosed herein and/or complement C1 inhibitor compared to a normal individual.

Another illustrative embodiment of the invention is an ELISA kit to screen for a plasma molecular profile in a patient that is associated with acute cellular renal allograft rejection by detecting α-1 anti-chymotrypsin and/or Apo A1 and/or the 5191 peptide disclosed herein and/or complement C1 inhibitor in plasma or serum, the kit comprising: (a) a microtiter plate coated with polyclonal or monoclonal antibodies specific to α-1 anti-chymotrypsin and/or Apo A1 and/or the 5191 peptide disclosed herein and/or complement C1 inhibitor; (b) polyclonal or monoclonal antibody-alkaline phosphatase conjugates reactive with α-1 anti-chymotrypsin and/or Apo A1 and/or the 5191 peptide disclosed herein and/or complement C1 inhibitor; (c) p-nitrophenyl-phosphate; and (d) α-1 anti-chymotrypsin and/or Apo A1 and/or the 5191 peptide disclosed herein and/or complement C1 inhibitor as an antigen standard.

BRIEF DESCRIPTION OF THE FIGURES

FIGS. 1A-1C: Candidate plasma proteins which detect renal allograft rejection. (1A) Classification and Regression Tree (CART) analysis assessing the biomarker candidates for detecting rejection vs. postrejection samples. (1B) Box plots of the adjusted intensities of the 4467 Da and 5191 Da biomarker candidates in rejection (group A, n=17), postrejection (group B, n=17), and nonrejection (group C, n=48) plasma samples. (1C) Box plots of the serum creatinine levels measured at the time of biopsy for rejection patients at the time of rejection and postrejection (n=16) compared with biopsy-proven nonrejection patients (n=19).

FIGS. 2A-2D: Identification of the C-terminal fragment of α-1 antichymotrypsin and apolipoprotein A1 (Apo A1). (2A) High-resolution MALDI-TOF mass spectrum of C8 high-performance liquid chromatography (HPLC)-purified fraction containing the 4467 Da biomarker candidate peptide (average mass as measured by SELDI-TOF MS). Monoisotopic mass differences indicate a sequence ladder of SALV (S, serine; A, alanine; L, leucine; and V, valine). (2B) Immunoprecipitation of plasma samples with monoclonal antibody against α-1-antichymotrypsin. Numbered peptides with average masses (Da) are presented. (2C) Immunoprecipitation of plasma samples with a monoclonal antibody against human Apo A1. (2D) Box plots of the SELDI adjusted peak intensities of Apo A1 in rejection (group A, n=17), postrejection (group B, n=17) and nonrejection (group C, n=48) plasma samples.

DETAILED DESCRIPTION OF THE INVENTION

Figure 2B:
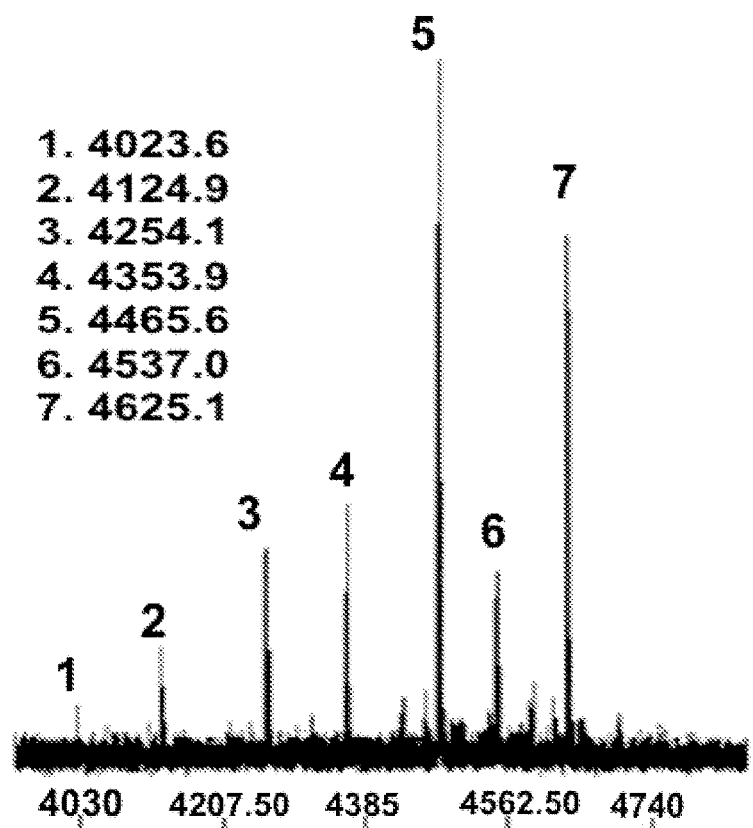

The invention described herein is based on the discovery that specific protein markers present in human plasma can be used to detect, predict and monitor transplant rejection. Assessment of the change in the levels of these proteins identifies patients at risk of rejection.

Definitions

All scientific and technical terms used in this application have meanings commonly used in the art unless otherwise specified. As used in this application, the following words or phrases have the meanings specified.

As used herein, a "sample" from a subject means a specimen obtained from the subject that contains plasma, blood, serum, saliva, urine, or other bodily fluid.

As used herein, the term "subject" includes any human or non-human animal. The term "non-human animal" includes all vertebrates, e.g., mammals and non-mammals, such as non-human primates, horses, sheep, dogs, cows, pigs, chickens, amphibians, reptiles, rodents etc. In a typical embodiment, the subject, or patient, is a human.

As used herein, a "control" sample means a sample that is representative of normal measures of the respective marker, or a baseline amount of marker to be used for comparison. Typically, the baseline will be a measurement taken from the same subject or patient. The sample can be an actual sample used for testing, or a reference level or range, based on known normal measurements of the corresponding marker.

As used herein, "5 kiloDalton (kDa) fragment of complement C4 anaphylatoxin (C4A)" refers to a fragment of C4A that is approximately 5 kDa in molecular weight, and includes a 5,051 Da C4A fragment that corresponds to SEQ ID NO: 3, and a 5,191 Da C4A fragment that corresponds to SEQ ID NO: 2. In some embodiments, the 5 kDa fragment of C4A is the 5,191 Da fragment.

As used herein, "a" or "an" means at least one, unless clearly indicated otherwise.

Markers & Methods

The invention provides a set of protein markers and methods of using these markers for assessment of a patient's immune status and for predicting rejection of an organ transplant. The markers include complement C4 anaphylatoxin (C4A), Apolipoprotein A1 (ApoA1), α-1 anti-chymotrypsin C terminal fragment (AACT), C1 protease inhibitor (C-inh), Serum Amyloid A (SAA), C-reactive Protein (CRP), Apolipoprotein E (ApoE), alpha-1-antitrypsin (A1AT), Post-translational modified ApoA1, Inter-alpha-trypsin inhibitor heavy chain H4 (ITIH4), and Alpha-2-macroglobulin (A2M), as well fragments of these proteins (see Tables 1 and 4, and SEQ ID NOs: 1-18). Changes in the levels of these markers in a patient's plasma or other bodily fluid are predictive of allograft rejection.

TABLE 1

Markers of Allograft Rejection

| m/z (Da) | SEQ ID NO: | Identity |
|---|---|---|
| 2,505 | 11 | Alpha-1-antitrypsin C-Terminal fragment (A1AT; amino acids 397-418) |
| 4,125 | 5 | Apolipoprotein A1 fragment (Apo A1; amino acids 148-183) |
| 4,187 | 13 | Plasma protease C1 inhibitor fragment (C1 inh; amino acids 445-478) |
| 4,467 | 8 | Alpha-1-antichymotrypsin C-terminal fragment (AACT; aa 385-422) |
| 5,051 | 3 | Complement C4 Anaphylatoxin (C4A; amino acids 698-742) |
| 5,191 | 2 | Complement C4 Anaphylatoxin (C4A; amino acids 702-746) |
| 11,694 | 14 | Serum Amyloid A (SAA) |
| 19,409 | 15 | C-reactive protein (CRP) |
| 28,077 | 6 | Apolipoprotein A1 (Apo A1) |
| 28,186 | 6 | Post-translational modified Apo A1 |
| 28,336 | 6 | Post-translational modified Apo A1 |
| 28,574 | 6 | Post-translational modified Apo A1 |
| 29,134 | 6 | Post-translational modified Apo A1 |
| 36,747 | 16 | Apolipoprotein E (Apo E) |
| 50,835 | 10 | Alpha-1-antitrypsin (A1AT) |
| 64,932 | 10 | Alpha-1-antitrypsin (A1AT) |
| 109,796 | 17 | Inter-alpha-trypsin inhibitor heavy chain H4 (ITIH4) |
| 143,718 | 18 | Alpha-2-macroglobulin (A2M or Alpha-2-M) |
| 188,758 | 18 | Alpha-2-macroglobulin (A2M or Alpha-2-M) |

The invention provides a method for detecting susceptibility in a patient to solid organ graft rejection. In one embodiment, the method detects susceptibility to rejection with greater than 80% sensitivity and specificity, and in a typical embodiment, with at least 90% sensitivity and at least 90% specificity. In one embodiment, the method comprises the steps of: (a) measuring the amount of a 5 kilo-Dalton (kDa) fragment of complement C4 anaphylatoxin (C4A) in a sample obtained from the patient; (b) comparing the amount of the 5 kDa fragment of C4A in the patient sample with the amount in a control sample; and (c) detecting susceptibility to graft rejection when the comparing shows an increase in the 5 kDa fragment of C4A in the patient sample relative to the control sample. In another embodiment, the method comprises the steps of: (a) contacting a sample obtained from the patient with a reagent that specifically binds a 5 kiloDalton (kDa) fragment of complement C4 anaphylatoxin (C4A); (b) measuring the amount of specific binding between the reagent and the patient sample; (c) comparing the amount of specific binding in (b) with the amount of specific binding of the reagent in a control sample; and (d) detecting susceptibility to graft rejection when the comparing in (c) shows an increase in specific binding to the 5 kDa fragment of C4A in the patient sample relative to the control sample. In one embodiment, the contacting further comprises contacting the patient sample with a reagent that binds Apolipoprotein A1 (ApoA1) and/or α-1 anti-chymotrypsin C terminal fragment (AACT), and the detecting further comprises detecting susceptibility to graft rejection when the comparing shows a decrease in the amount of ApoA1 and/or AACT in the patient sample relative to the control sample. In one embodiment, the contacting and comparing comprise contacting the patient sample with reagents that bind ApoA1 and AACT.

In another embodiment, the invention provides a method for detecting susceptibility in a patient to solid organ graft rejection. In one embodiment, the method comprises the steps of: (a) contacting a sample obtained from the patient with a reagent that specifically binds a set of biomarkers comprising two or more markers listed in Table 1; (b) measuring the amount of specific binding between the reagents and the patient sample; (c) comparing the amount of specific binding in (b) with the amount of specific binding of the reagents in a control sample; and (d) detecting susceptibility to graft rejection when the comparing in (c) shows a significant increase or decrease in specific binding to the biomarkers in the patient sample relative to the control sample. In some embodiments, steps (a)-(c) are performed for 2, 3, 4, 5, 6, 7, 8, 9, 10, 12, 15, up to 19 of the markers listed in Table 1. In one embodiment, the set of markers consists of 8 or fewer markers listed in Table 1. In another embodiment, the set of markers consists of 6 or fewer markers listed in Table 1. In yet another embodiment, the set of markers consists of 4 or fewer markers listed in Table 1.

With respect to the following markers, susceptibility to graft rejection is detected when the specific binding of reagent to marker is increased relative to the control: C4A, C1 protease inhibitor (C1-inh), Serum Amyloid A (SAA), C-reactive Protein (CRP), Apolipoprotein E (ApoE), alpha-1-antitrypsin (A1AT), including fragments thereof, and/or specific binding of reagent to the following markers is decreased relative to control: AACT, ApoA1, Post-translational modified ApoA1, Inter-alpha-trypsin inhibitor heavy chain H4 (ITIH4), Alpha-2-macroglobulin (A2M), including fragments thereof. In a typical embodiment, the difference is a decrease or increase of at least 10% relative to the control.

In another embodiment, the invention provides a method for detecting susceptibility in a patient to solid organ graft rejection, the method comprising the steps of: (a) contacting a sample obtained from the patient with reagents that specifically bind a set of markers consisting of: a 5191 Dalton fragment of complement C4 anaphylatoxin (C4A), α-1 anti-chymotrypsin C terminal fragment (AACT), and Apo A1; and optionally further consisting of: complement C1 inhibitor, and/or a marker listed in Table 1; (b) measuring the amount of specific binding between the reagent and the sample; (c) comparing the amount of specific binding in (b) with the amount of specific binding of the reagent to a control sample; and (d) detecting susceptibility to graft rejection when the comparing in (c) shows an increase in the 5191 Dalton fragment of C4A or a decrease AACT and/or ApoA1 relative to the control sample.

In some embodiments, the measuring comprises an immunoassay. In other embodiments, the measuring comprises mass spectrometry. Other assay methods include fluorescence activated cell sorting (FACS), western blotting, and amplification of a surrogate DNA template. Representative examples of reagents include, but are not limited to, an antibody, a nucleic acid probe, or a synthetic probe. The probe or antibody may optionally be labeled with a detectable marker. In some embodiments, the reagents are labeled with a detectable marker and/or observed using a chromogenic or fluorogenic substrate.

Examples of solid organ grafts include, but are not limited to, kidney, liver, heart, pancreas, lung, intestine and thymus. In one embodiment, the solid organ graft rejection is acute cellular renal allograft rejection. Other types of solid organ graft rejection include chronic rejection, such as chronic allograft nephropathy, or interstitial fibrosis with tubular atrophy.

Additionally provided is a method for detecting susceptibility in a patient to solid organ graft rejection, the method comprising the steps of: (a) contacting a sample obtained from the patient with a reagent that specifically binds complement C4 anaphylatoxin (C4A); (b) measuring the amount of specific binding between the reagent and the sample; (c) comparing the amount of specific binding in (b) with a control sample; wherein a greater amount of binding in (b) relative to the control is indicative of susceptibility to solid organ graft rejection.

Another illustrative embodiment of the invention is a mass spectrometry assay to identify the peptide and/or protein profile in a patient that is associated with solid organ allograft rejection by detecting α-1 anti-chymotrypsin and/or Apo A1 and/or C4A and/or complement C1 inhibitor and/or one of the other 16 proteins in Table 1 in plasma or serum or other body fluid, the assay comprising the steps of: (a) measuring the specific amount of specific peptide by mass spectrometry in plasma, serum or other body fluid; (b) comparing the specific quantity of protein/peptide in (a) with a control sample; wherein a greater or lesser amount of specific peptide relative to the control is indicative of susceptibility to solid organ graft rejection.

Also provided is a method for detecting susceptibility in a patient to acute cellular renal allograft rejection, the method comprising the steps of: (a) providing polyclonal or monoclonal antibodies against α-1 anti-chymotrypsin and/or Apo A1 and/or C4A and/or complement C1 inhibitor; (b) providing a microtiter plate coated with the antibodies; (c) adding the serum or plasma to the microtiter plate; (d) providing alkaline phosphatase-antibody conjugates reactive with α-1 anti-chymotrypsin and/or Apo A1 and/or C4A and/or complement C1 inhibitor to the microtiter plate; (e) providing p-nitrophenyl-phosphate to the microtiter plate; and (f) comparing the reaction which occurs as a result of steps (a) to (e) with a standard curve to determine the levels of α-1 anti-chymotrypsin and/or Apo A1 and/or C4A and/or complement C1 inhibitor compared to a normal individual.

Embodiments of the invention provide assays and methods for the detection and/or quantitation in a sample of: AACT and/or Apo A1 and/or C4A and/or SAA and/or CRP and/or A2M and/or ApoE and/or ITIH4 and/or A1AT and/or C-inh and/or fragments of these polypeptides. Typical embodiments of the invention utilize ELISA-type assays of the type that are suitable for use with biological fluid samples such as blood, plasma, serum, or other bodily fluids of a mammal, particularly a human. Methodological embodiments include testing for the amounts of AACT and/or C4A and/or Apo A1 polypeptides, fragments of these markers, and/or a combination of the markers described herein in biological fluid samples. Certain embodiments examine together: α-1 antichymotrypsin, Apo A1, complement C1 inhibitor and the 5191 Da peptide of C4A in order to, for example, identify a plasma molecular profile in a patient that is associated with acute cellular renal allograft rejection. Certain embodiments examine 1 (e.g. the 5191 Da C4A peptide) or 2 (e.g. C4A peptide plus α-1 antichymotrypsin or Apo A1) or 3 (e.g. α-1 antichymotrypsin, Apo A1 and the 5191 Da C4A peptide) or all 4 of these biomarkers.

In certain embodiments of the invention, the 5191 Da C4A peptide is purified and this purified peptide is then injected into animals such as a rabbits to generate polyclonal antibodies specific to the 5191 Da peptide that can be used in ELISA tests or the like. Similarly, monoclonal antibody preparations to the protein may be prepared by injecting the purified 5191 Da peptide into mice, harvesting the spleen and lymph node cells, fusing these cells with mouse myeloma cells and using the resultant hybridoma cells to produce the monoclonal antibody.

One illustrative embodiment of the invention is a method for detecting α-1 anti-chymotrypsin and/or Apo A1 and/or the 5191 peptide disclosed herein and/or complement C1 inhibitor in plasma to screen for a plasma molecular profile in a patient that is associated with acute cellular renal allograft rejection comprising the steps of: (a) providing polyclonal or monoclonal antibodies against α-1 anti-chymotrypsin and/or Apo A1 and/or the 5191 peptide disclosed herein and/or complement C1 inhibitor; (b) providing a microtiter plate coated with the antibodies; (c) adding the serum or plasma to the microtiter plate; (d) providing alkaline phosphatase-antibody conjugates reactive with α-1 anti-chymotrypsin and/or Apo A1 and/or the 5191 peptide disclosed herein and/or complement C1 inhibitor to the microtiter plate; (e) providing p-nitrophenyl-phosphate to the microtiter plate; and (f) comparing the reaction which occurs as a result of steps (a) to (e) with a standard curve to determine the levels of α-1 anti-chymotrypsin and/or Apo A1 and/or the 5191 peptide disclosed herein and/or complement C1 inhibitor compared to a normal individual.

An amount of marker is considered increased or decreased if it differs by a statistically significant amount from the amount present in the control. In some embodiments, the difference is an increase or decrease of at least 10%; in other embodiments, the difference is at least 20%, 30%, 40%, 50% or more. In other embodiments, a reference range has been identified for the amount of the marker present in a normal, control sample, and a test sample having an amount of the marker that is outside the reference range for that marker is susceptible to rejection. In a typical embodiment, the sample is a plasma sample. Other bodily fluids can be used for the sample, including serum, urine and saliva.

The following combinations of markers are contemplated for use with the methods of the invention: C4A, ApoA1; C4A, AACT; C4A, A1AT; C4A, C1-inh; C4A, SAA; C4A, CRP; C4A, ApoE; C4A, ITIH4; C4A, A2M; ApoA1, A1AT; ApoA1, C1-inh; ApoA1, SAA; ApoA1, CRP; ApoA1, ApoE; ApoA1, ITIH4; ApoA1, A2M; AACT, A1AT; AACT, C1-inh; AACT, SAA; AACT, CRP; AACT, ApoE; AACT, ITIH4; AACT, A2M; A1AT, C1-inh; A1AT, SAA; A1AT, CRP; A1AT, ApoE; A1AT, ITIH4; A1AT, A2M; C1-inh, SAA; C1-inh, CRP; C1-inh, ApoE; C1-inh, ITIH4; C1-inh, A2M; SAA, CRP; SAA, ApoE; SAA, ITIH4; SAA, A2M; CRP, ApoE; CRP, ITIH4; CRP, A2M; ApoE, ITIH4; ApoE, A2M; ITIH4, A2M; C4A, ApoA1, AACT; C4A, ApoA1, A1AT; C4A, ApoA1, C1-inh; C4A, ApoA1, SAA; C4A, ApoA1, CRP; C4A, ApoA1, ApoE; C4A, ApoA1, ITIH4; C4A, ApoA1, A2M; C4A, AACT, A1AT; C4A, AACT, C1-inh; C4A, AACT, SAA; C4A, AACT, CRP; C4A, AACT, ApoE; C4A, AACT, ITIH4; C4A, AACT, A2M; C4A, A1AT, C1-inh; C4A, A1AT, SAA; C4A, A1AT, CRP; C4A, A1AT, ApoE; C4A, A1AT, ITIH4; C4A, A1AT, A2M; C4A, C1-inh, SAA; C4A, C1-inh, CRP; C4A, C1-inh, ApoE; C4A, C1-inh, ITIH4; C4A, C1-inh, A2M; C4A, SAA, CRP; C4A, SAA, ApoE; C4A, SAA, ITIH4; C4A, SAA, A2M; C4A, CRP, ApoE; C4A, CRP, ITIH4; C4A, CRP, A2M; C4A, ApoE, ITIH4; C4A, ApoE, A2M; C4A, ITIH4, A2M; ApoA1, AACT, A1AT; ApoA1, AACT, C1-inh; ApoA1, AACT, ApoE; ApoA1, AACT, ITIH4; ApoA1, AACT, A2M; ApoA1, A1AT, C1-inh; ApoA1, A1AT, SAA; ApoA1, A1AT, CRP; ApoA1, A1AT, ApoE; ApoA1, A1AT, ITIH4; ApoA1, A1AT, A2M; ApoA1, C1-inh, SAA; ApoA1, C1-inh, CRP; ApoA1, C1-inh, ApoE; ApoA1, C1-inh, ITIH4; ApoA1, C1-inh, A2M; ApoA1, SAA, CRP; ApoA1, SAA, ApoE; ApoA1, SAA, ITIH4; ApoA1, SAA, A2M; ApoA1, CRP, ApoE; ApoA1, CRP, ITIH4; ApoA1, CRP, A2M; ApoA1, ApoE, ITIH4; ApoA1, ApoE, A2M; ApoA1, ITIH4, A2M; AACT, A1AT, C1-inh; AACT, A1AT, ApoE; AACT, A1AT, ITIH4; AACT, C1-inh, SAA; AACT, C1-inh, CRP; AACT, C1-inh, ApoE; AACT, C1-inh, ITIH4; AACT, C1-inh, A2M; AACT, SAA, CRP; AACT, SAA, ApoE; AACT, SAA, ITIH4; AACT, SAA, A2M; AACT, CRP, ApoE; AACT, CRP, ITIH4; AACT, CRP, A2M; AACT, ApoE, ITIH4; AACT, ApoE, A2M; AACT, ITIH4, A2M; A1AT, C1-inh, SAA; A1AT, C1-inh, CRP; A1AT, C1-inh, ApoE; A1AT, C1-inh, ITIH4; A1AT, C1-inh, A2M; A1AT, SAA, CRP; A1AT, SAA, ApoE; A1AT, SAA, ITIH4; A1AT, SAA, A2M; A1AT, CRP, ApoE; A1AT, CRP, ITIH4; A1AT, CRP, A2M; A1AT, ApoE, ITIH4; A1AT, ApoE, A2M; A1AT, ITIH4, A2M; C1-inh, SAA, CRP; C1-inh, SAA, ApoE; C1-inh, SAA, ITIH4; C1-inh, SAA, A2M; C1-inh, CRP, ApoE; C1-inh, CRP, ITIH4; C1-inh, CRP, A2M; C1-inh, ApoE, ITIH4; C1-inh, ApoE, A2M; C1-inh, ITIH4, A2M; SAA, CRP, ApoE; SAA, CRP, ITIH4; SAA, CRP, A2M; SAA, ApoE, ITIH4; SAA, ApoE, A2M; SAA, ITIH4, A2M; CRP, ApoE, ITIH4; CRP, ApoE, A2M; CRP, ITIH4, A2M; ApoE, ITIH4, A2M; C4A, ApoA1, AACT, A1AT; C4A, ApoA1, AACT, C1-inh; C4A, ApoA1, AACT, SAA; C4A, ApoA1, AACT, CRP; C4A, ApoA1, AACT, ApoE; C4A, ApoA1, AACT, ITIH4; C4A, ApoA1, AACT, A2M; C4A, ApoA1, A1AT, C1-inh; C4A, ApoA1, A1AT, SAA; C4A, ApoA1, A1AT, CRP; C4A, ApoA1, A1AT, ApoE; C4A, ApoA1, A1AT, ITIH4; C4A, ApoA1, A1AT, A2M; C4A, ApoA1, C1-inh, SAA; C4A, ApoA1, C1-inh, CRP; C4A, ApoA1, C1-inh, ApoE; C4A, ApoA1, C1-inh, ITIH4; C4A, ApoA1, C1-inh, A2M; C4A, ApoA1, SAA, CRP; C4A, ApoA1, SAA, ApoE; C4A, ApoA1, SAA, ITIH4; C4A, ApoA1, SAA, A2M; C4A, ApoA1, CRP, ApoE; C4A, ApoA1, CRP, ITIH4; C4A, ApoA1, CRP, A2M; C4A, ApoA1, ApoE, ITIH4; C4A, ApoA1, ApoE, A2M; C4A, ApoA1, ITIH4, A2M; C4A, AACT, A1AT, C1-inh; C4A, AACT, A1AT, SAA; C4A, AACT, A1AT, CRP; C4A, AACT, A1AT, ApoE; C4A, AACT, A1AT, ITIH4; C4A, AACT, A1AT, A2M; C4A, AACT, C1-inh, SAA; C4A, AACT, C1-inh, CRP; C4A, AACT, C1-inh, ApoE; C4A, AACT, C1-inh, ITIH4; C4A, AACT, C1-inh, A2M; C4A, AACT, SAA, CRP; C4A, AACT, SAA, ApoE; C4A, AACT, SAA, ITIH4; C4A, AACT, SAA, A2M; C4A, AACT, CRP, ApoE; C4A, AACT, CRP, ITIH4; C4A, AACT, CRP, A2M; C4A, AACT, ApoE, ITIH4; C4A, AACT, ApoE, A2M; C4A, AACT, ITIH4, A2M; C4A, A1AT, C1-inh, SAA; C4A, A1AT, C1-inh, CRP; C4A, A1AT, C1-inh, ApoE; C4A, A1AT, C1-inh, ITIH4; C4A, A1AT, C1-inh, A2M; C4A, A1AT, SAA, CRP; C4A, A1AT, SAA, ApoE; C4A, A1AT, SAA, ITIH4; C4A, A1AT, SAA, A2M; C4A, A1AT, CRP, ApoE; C4A, A1AT, CRP, ITIH4; C4A, A1AT, CRP, A2M; C4A, A1AT, ApoE, ITIH4; C4A, A1AT, ApoE, A2M; C4A, A1AT, ITIH4, A2M; C4A, C1-inh, SAA, CRP; C4A, C1-inh, SAA, ApoE; C4A, C1-inh, SAA, ITIH4; C4A, C1-inh, SAA, A2M; C4A, C1-inh, CRP, ApoE; C4A, C1-inh, CRP, ITIH4; C4A, C1-inh, CRP, A2M; C4A, C1-inh, ApoE, ITIH4; C4A, C1-inh, ApoE, A2M; C4A, C1-inh, ITIH4, A2M; C4A, SAA, CRP, ApoE; C4A, SAA, CRP, ITIH4; C4A, SAA, CRP, A2M; C4A, SAA, ApoE, ITIH4; C4A, SAA, ApoE, A2M; C4A, SAA, ITIH4, A2M; C4A, CRP, ApoE, ITIH4; C4A, CRP, ApoE, A2M; C4A, CRP, ITIH4, A2M; C4A, ApoE, ITIH4, A2M; ApoA1, AACT, A1AT, C1-inh; ApoA1, AACT, A1AT, SAA; ApoA1, AACT, A1AT, CRP; ApoA1, AACT, A1AT, ApoE; ApoA1, AACT, A1AT, ITIH4; ApoA1, AACT, A1AT, A2M; ApoA1, AACT, C1-inh, SAA; ApoA1, AACT, C1-inh, CRP; ApoA1, AACT, C1-inh, ApoE; ApoA1, AACT, C1-inh, ITIH4; ApoA1, AACT, C1-inh, A2M; ApoA1, AACT, SAA, ApoE; ApoA1, AACT, SAA, ITIH4; ApoA1, AACT, SAA, A2M; ApoA1, AACT, CRP, ApoE; ApoA1, AACT, CRP, ITIH4; ApoA1, AACT, CRP, A2M; ApoA1, AACT, ApoE, ITIH4; ApoA1, AACT, ApoE, A2M; ApoA1, AACT, ITIH4, A2M; ApoA1, A1AT, C1-inh, SAA; ApoA1, A1AT, C1-inh, CRP; ApoA1, A1AT, C1-inh, ApoE; ApoA1, A1AT, C1-inh, ITIH4; ApoA1, A1AT, C1-inh, A2M; ApoA1, A1AT, SAA, CRP; ApoA1, A1AT, SAA, ApoE; ApoA1, A1AT, SAA, ITIH4; ApoA1, A1AT, SAA, A2M; ApoA1, A1AT, CRP, ApoE; ApoA1, A1AT, CRP, ITIH4; ApoA1, A1AT, CRP, A2M; ApoA1, A1AT, ApoE, ITIH4; ApoA1, A1AT, ApoE, A2M; ApoA1, A1AT, ITIH4, A2M; ApoA1, C1-inh, SAA, CRP; ApoA1, C1-inh, SAA, ApoE; ApoA1, C1-inh, SAA, ITIH4; ApoA1, C1-inh, SAA, A2M; ApoA1, C1-inh, CRP, ApoE; ApoA1, C1-inh, CRP, ITIH4; ApoA1, C1-inh, CRP, A2M; ApoA1, C1-inh, ApoE, ITIH4; ApoA1, C1-inh, ApoE, A2M; ApoA1, C1-inh, ITIH4, A2M; ApoA1, SAA, CRP, ApoE; ApoA1, SAA, CRP, ITIH4; ApoA1, SAA, CRP, A2M; ApoA1, SAA, ApoE, ITIH4; ApoA1, SAA, ApoE, A2M; ApoA1, SAA, ITIH4, A2M; ApoA1, CRP, ApoE, ITIH4; ApoA1, CRP, ApoE, A2M; ApoA1, CRP, ITIH4, A2M; ApoA1, ApoE, ITIH4, A2M; AACT, A1AT, C1-inh, SAA; AACT, A1AT, C1-inh, CRP; AACT, A1AT, C1-inh, ApoE; AACT, A1AT, C1-inh, ITIH4; AACT, A1AT, C1-inh, A2M; AACT, A1AT, SAA, ApoE; AACT, A1AT, SAA, ITIH4; AACT, A1AT, CRP, ApoE; AACT, A1AT, CRP, ITIH4; AACT, A1AT, ApoE, ITIH4; AACT, A1AT, ApoE, A2M; AACT, A1AT, ITIH4, A2M; AACT, C1-inh, SAA, CRP; AACT, C1-inh, SAA, ApoE; AACT, C1-inh, SAA, ITIH4; AACT, C1-inh, SAA, A2M; AACT, C1-inh, CRP, ApoE; AACT, C1-inh, CRP, ITIH4; AACT, C1-inh, CRP, A2M; AACT, C1-inh, ApoE, ITIH4; AACT, C1-inh, ApoE, A2M; AACT, C1-inh, ITIH4, A2M; AACT, SAA, CRP, ApoE; AACT, SAA, CRP, ITIH4; AACT, SAA, CRP, A2M; AACT, SAA, ApoE, ITIH4; AACT, SAA, ApoE, A2M; AACT, SAA, ITIH4, A2M; AACT, CRP, ApoE, ITIH4; AACT, CRP, ApoE, A2M; AACT, CRP, ITIH4, A2M; AACT, ApoE, ITIH4, A2M; A1AT, C1-inh, SAA, CRP; A1AT, C1-inh, SAA, ApoE; A1AT, C1-inh, SAA, ITIH4; A1AT, C1-inh, SAA, A2M; A1AT, C1-inh, CRP, ApoE; A1AT, C1-inh, CRP, ITIH4; A1AT, C1-inh, CRP, A2M; A1AT, C1-inh, ApoE, ITIH4; A1AT, C1-inh, ApoE, A2M; A1AT, C1-inh, ITIH4, A2M; A1AT, SAA, CRP, ApoE; A1AT, SAA, CRP, ITIH4; A1AT, SAA, CRP, A2M; A1AT, SAA, ApoE, ITIH4; A1AT, SAA, ApoE, A2M; A1AT, SAA, ITIH4, A2M; A1AT, CRP, ApoE, ITIH4; A1AT, CRP, ApoE, A2M; A1AT, CRP, ITIH4, A2M; A1AT, ApoE, ITIH4, A2M; C1-inh, SAA, CRP, ApoE; C1-inh, SAA, CRP, ITIH4; C1-inh, SAA, CRP, A2M; C1-inh, SAA, ApoE, ITIH4; C1-inh, SAA, ApoE, A2M; C1-inh, SAA, ITIH4, A2M; C1-inh, CRP, ApoE, ITIH4; C1-inh, CRP, ApoE, A2M; C1-inh, CRP, ITIH4, A2M; C1-inh, ApoE, ITIH4, A2M; SAA, CRP, ApoE, ITIH4; SAA, CRP, ApoE, A2M; SAA, CRP, ITIH4, A2M; SAA, ApoE, ITIH4, A2M; CRP, ApoE, ITIH4, A2M; C4A, ApoA1, AACT, A1AT, C1-inh; C4A, ApoA1, AACT, A1AT, SAA; C4A, ApoA1, AACT, A1AT, CRP; C4A, ApoA1, AACT, A1AT, ApoE; C4A, ApoA1, AACT, A1AT, ITIH4; C4A, ApoA1, AACT, A1AT, A2M; C4A, ApoA1, AACT, C1-inh, SAA; C4A, ApoA1, AACT, C1-inh, CRP; C4A, ApoA1, AACT, C1-inh, ApoE; C4A, ApoA1, AACT, C1-inh, ITIH4; C4A, ApoA1, AACT, C1-inh, A2M; C4A, ApoA1, AACT, SAA, CRP; C4A, ApoA1, AACT, SAA, ApoE; C4A, ApoA1, AACT, SAA, ITIH4; C4A, ApoA1, AACT, SAA, A2M; C4A, ApoA1, AACT, CRP, ApoE; C4A, ApoA1, AACT, CRP, ITIH4; C4A, ApoA1, AACT, CRP, A2M; C4A, ApoA1, AACT, ApoE, ITIH4; C4A, ApoA1, AACT, ApoE, A2M; C4A, ApoA1, AACT, ITIH4, A2M; C4A, ApoA1, A1AT, C1-inh, SAA; C4A, ApoA1, A1AT, C1-inh, CRP; C4A, ApoA1, A1AT, C1-inh, ApoE; C4A, ApoA1, A1AT, C1-inh, ITIH4; C4A, ApoA1, A1AT, C1-inh, A2M; C4A, ApoA1, A1AT, SAA, CRP; C4A, ApoA1, A1AT, SAA, ApoE; C4A, ApoA1, A1AT, SAA, ITIH4; C4A, ApoA1, A1AT, SAA, A2M; C4A, ApoA1, A1AT, CRP, ApoE; C4A, ApoA1, A1AT, CRP, ITIH4; C4A, ApoA1, A1AT, CRP, A2M; C4A, ApoA1, A1AT, ApoE, ITIH4; C4A, ApoA1, A1AT, ApoE, A2M; C4A, ApoA1, A1AT, ITIH4, A2M; C4A, ApoA1, C1-inh, SAA, CRP; C4A, ApoA1, C1-inh, SAA, ApoE; C4A, ApoA1, C1-inh, SAA, ITIH4; C4A, ApoA1, C1-inh, SAA, A2M; C4A, ApoA1, C1-inh, CRP, ApoE; C4A, ApoA1, C1-inh, CRP, ITIH4; C4A, ApoA1, C1-inh, CRP, A2M; C4A, ApoA1, C1-inh, ApoE, ITIH4; C4A, ApoA1, C1-inh, ApoE, A2M; C4A, ApoA1, C1-inh, ITIH4, A2M; C4A, ApoA1, SAA, CRP, ApoE; C4A, ApoA1, SAA, CRP, ITIH4; C4A, ApoA1, SAA, CRP, A2M; C4A, ApoA1, SAA, ApoE, ITIH4; C4A, ApoA1, SAA, ApoE, A2M; C4A, ApoA1, SAA, ITIH4, A2M; C4A, ApoA1, CRP, ApoE, ITIH4; C4A, ApoA1, CRP, ApoE, A2M; C4A, ApoA1, CRP, ITIH4, A2M; C4A, ApoA1, ApoE, ITIH4, A2M; C4A, AACT, A1AT, C1-inh, SAA; C4A, AACT, A1AT, C1-inh, CRP; C4A, AACT, A1AT, C1-inh, ApoE; C4A, AACT, A1AT, C1-inh, ITIH4; C4A, AACT, A1AT, C1-inh, A2M; C4A, AACT, A1AT, SAA, CRP; C4A, AACT, A1AT, SAA, ApoE; C4A, AACT, A1AT, SAA, ITIH4; C4A, AACT, A1AT, SAA, A2M; C4A, AACT, A1AT, CRP, ApoE; C4A, AACT, A1AT, CRP, ITIH4; C4A, AACT, A1AT, CRP, A2M; C4A, AACT, A1AT, ApoE, ITIH4; C4A, AACT, A1AT, ApoE, A2M; C4A, AACT, A1AT, ITIH4, A2M; C4A, AACT, C1-inh, SAA, CRP; C4A, AACT, C1-inh, SAA, ApoE; C4A, AACT, C1-inh, SAA, ITIH4; C4A, AACT, C1-inh, SAA, A2M; C4A, AACT, C1-inh, CRP, ApoE; C4A, AACT, C1-inh, CRP, ITIH4; C4A, AACT, C1-inh, CRP, A2M; C4A, AACT, C1-inh, ApoE, ITIH4; C4A, AACT, C1-inh, ApoE, A2M; C4A, AACT, C1-inh, ITIH4, A2M; C4A, AACT, SAA, CRP, ApoE; C4A, AACT, SAA, CRP, ITIH4; C4A, AACT, SAA, CRP, A2M; C4A, AACT, SAA, ApoE, ITIH4; C4A, AACT, SAA, ApoE, A2M; C4A, AACT, SAA, ITIH4, A2M; C4A, AACT, CRP, ApoE, ITIH4; C4A, AACT, CRP, ApoE, A2M; C4A, AACT, CRP, ITIH4, A2M; C4A, AACT, ApoE, ITIH4, A2M; C4A, A1AT, C1-inh, SAA, CRP; C4A, A1AT, C1-inh, SAA, ApoE; C4A, A1AT, C1-inh, SAA, ITIH4; C4A, A1AT, C1-inh, SAA, A2M; C4A, A1AT, C1-inh, CRP, ApoE; C4A, A1AT, C1-inh, CRP, ITIH4; C4A, A1AT, C1-inh, CRP, A2M; C4A, A1AT, C1-inh, ApoE, ITIH4; C4A, A1AT, C1-inh, ApoE, A2M; C4A, A1AT, C1-inh, ITIH4, A2M; C4A, A1AT, SAA, CRP, ApoE; C4A, A1AT, SAA, CRP, ITIH4; C4A, A1AT, SAA, CRP, A2M; C4A, A1AT, SAA, ApoE, ITIH4; C4A, A1AT, SAA, ApoE, A2M; C4A, A1AT, SAA, ITIH4, A2M; C4A, A1AT, CRP, ApoE, ITIH4; C4A, A1AT, CRP, ApoE, A2M; C4A, A1AT, CRP, ITIH4, A2M; C4A, A1AT, ApoE, ITIH4, A2M; C4A, C1-inh, SAA, CRP, ApoE; C4A, C1-inh, SAA, CRP, ITIH4; C4A, C1-inh, SAA, CRP, A2M; C4A, C1-inh, SAA, ApoE, ITIH4; C4A, C1-inh, SAA, ApoE, A2M; C4A, C1-inh, SAA, ITIH4, A2M; C4A, C1-inh, CRP, ApoE, ITIH4; C4A, C1-inh, CRP, ApoE, A2M; C4A, C1-inh, CRP, ITIH4, A2M; C4A, C1-inh, ApoE, ITIH4, A2M; C4A, SAA, CRP, ApoE, ITIH4; C4A, SAA, CRP, ApoE, A2M; C4A, SAA, CRP, ITIH4, A2M; C4A, SAA, ApoE, ITIH4, A2M; C4A, CRP, ApoE, ITIH4, A2M; ApoA1, AACT, A1AT, C1-inh, SAA; ApoA1, AACT, A1AT, C1-inh, CRP; ApoA1, AACT, A1AT, C1-inh, ApoE; ApoA1, AACT, A1AT, C1-inh, ITIH4; ApoA1, AACT, A1AT, C1-inh, A2M; ApoA1, AACT, A1AT, SAA, CRP; ApoA1, AACT, A1AT, SAA, ApoE; ApoA1, AACT, A1AT, SAA, ITIH4; ApoA1, AACT, A1AT, SAA, A2M; ApoA1, AACT, A1AT, CRP, ApoE; ApoA1, AACT, A1AT, CRP, ITIH4; ApoA1, AACT, A1AT, CRP, A2M; ApoA1, AACT, A1AT, ApoE, ITIH4; ApoA1, AACT, A1AT, ApoE, A2M; ApoA1, AACT, A1AT, ITIH4, A2M; ApoA1, AACT, C1-inh, SAA, CRP; ApoA1, AACT, C1-inh, SAA, ApoE; ApoA1, AACT, C1-inh, SAA, ITIH4; ApoA1, AACT, C1-inh, SAA, A2M; ApoA1, AACT, C1-inh, CRP, ApoE; ApoA1, AACT, C1-inh, CRP, ITIH4; ApoA1, AACT, C1-inh, CRP, A2M; ApoA1, AACT, C1-inh, ApoE, ITIH4; ApoA1, AACT, C1-inh, ApoE, A2M; ApoA1, AACT, C1-inh, ITIH4, A2M; ApoA1, AACT, SAA, CRP, ApoE; ApoA1, AACT, SAA, CRP, ITIH4; ApoA1, AACT, SAA, CRP, A2M; ApoA1, AACT, SAA, ApoE, ITIH4; ApoA1, AACT, SAA, ApoE, A2M; ApoA1, AACT, SAA, ITIH4, A2M; ApoA1, AACT, CRP, ApoE, ITIH4; ApoA1, AACT, CRP, ApoE, A2M; ApoA1, AACT, CRP, ITIH4, A2M; ApoA1, AACT, ApoE, ITIH4, A2M; ApoA1, A1AT, C1-inh, SAA, CRP; ApoA1, A1AT, C1-inh, SAA, ApoE; ApoA1, A1AT, C1-inh, SAA, ITIH4; ApoA1, A1AT, C1-inh, SAA, A2M; ApoA1, A1AT, C1-inh, CRP, ApoE; ApoA1, A1AT, C1-inh, CRP, ITIH4; ApoA1, A1AT, C1-inh, CRP, A2M; ApoA1, A1AT, C1-inh, ApoE, ITIH4; ApoA1, A1AT, C1-inh, ApoE, A2M; ApoA1, A1AT, C1-inh, ITIH4, A2M; ApoA1, A1AT, SAA, CRP, ApoE; ApoA1, A1AT, SAA, CRP, ITIH4; ApoA1, A1AT, SAA, CRP, A2M; ApoA1, A1AT, SAA, ApoE, ITIH4; ApoA1, A1AT, SAA, ApoE, A2M; ApoA1, A1AT, SAA, ITIH4, A2M; ApoA1, A1AT, CRP, ApoE, ITIH4; ApoA1, A1AT, CRP, ApoE, A2M; ApoA1, A1AT, CRP, ITIH4, A2M; ApoA1, A1AT, ApoE, ITIH4, A2M; ApoA1, C1-inh, SAA, CRP, ApoE; ApoA1, C1-inh, SAA, CRP, ITIH4; ApoA1, C1-inh, SAA, CRP, A2M; ApoA1, C1-inh, SAA, ApoE, ITIH4; ApoA1, C1-inh, SAA, ApoE, A2M; ApoA1, C1-inh, SAA, ITIH4, A2M; ApoA1, C1-inh, CRP, ApoE, ITIH4; ApoA1, C1-inh, CRP, ApoE, A2M; ApoA1, C1-inh, CRP, ITIH4, A2M; ApoA1, C1-inh, ApoE, ITIH4, A2M; ApoA1, SAA, CRP, ApoE, ITIH4; ApoA1, SAA, CRP, ApoE, A2M; ApoA1, SAA, CRP, ITIH4, A2M; ApoA1, SAA, ApoE, ITIH4, A2M; ApoA1, CRP, ApoE, ITIH4, A2M; AACT, A1AT, C1-inh, SAA, CRP; AACT, A1AT, C1-inh, SAA, ApoE; AACT, A1AT, C1-inh, SAA, ITIH4; AACT, A1AT, C1-inh, SAA, A2M; AACT, A1AT, C1-inh, CRP, ApoE; AACT, A1AT, C1-inh, CRP, ITIH4; AACT, A1AT, C1-inh, CRP, A2M; AACT, A1AT, C1-inh, ApoE, ITIH4; AACT, A1AT, C1-inh, ApoE, A2M; AACT, A1AT, C1-inh, ITIH4, A2M; AACT, A1AT, SAA, CRP, ApoE; AACT, A1AT, SAA, CRP, ITIH4; AACT, A1AT, SAA, CRP, A2M; AACT, A1AT, SAA, ApoE, ITIH4; AACT, A1AT, SAA, ApoE, A2M; AACT, A1AT, SAA, ITIH4, A2M; AACT, A1AT, CRP, ApoE, ITIH4; AACT, A1AT, CRP, ApoE, A2M; AACT, A1AT, CRP, ITIH4, A2M; AACT, A1AT, ApoE, ITIH4, A2M; AACT, C1-inh, SAA, CRP, ApoE; AACT, C1-inh, SAA, CRP, ITIH4; AACT, C1-inh, SAA, CRP, A2M; AACT, C1-inh, SAA, ApoE, ITIH4; AACT, C1-inh, SAA, ApoE, A2M; AACT, C1-inh, SAA, ITIH4, A2M; AACT, C1-inh, CRP, ApoE, ITIH4; AACT, C1-inh, CRP, ApoE, A2M; AACT, C1-inh, CRP, ITIH4, A2M; AACT, C1-inh, ApoE, ITIH4, A2M; AACT, SAA, CRP, ApoE, ITIH4; AACT, SAA, CRP, ApoE, A2M; AACT, SAA, CRP, ITIH4, A2M; AACT, SAA, ApoE, ITIH4, A2M; AACT, CRP, ApoE, ITIH4, A2M; A1AT, C1-inh, SAA, CRP, ApoE; A1AT, C1-inh, SAA, CRP, ITIH4; A1AT, C1-inh, SAA, CRP, A2M; A1AT, C1-inh, SAA, ApoE, ITIH4; A1AT, C1-inh, SAA, ApoE, A2M; A1AT, C1-inh, SAA, ITIH4, A2M; A1AT, C1-inh, CRP, ApoE, ITIH4; A1AT, C1-inh, CRP, ApoE, A2M; A1AT, C1-inh, CRP, ITIH4, A2M; A1AT, C1-inh, ApoE, ITIH4, A2M; A1AT, SAA, CRP, ApoE, ITIH4; A1AT, SAA, CRP, ApoE, A2M; A1AT, SAA, CRP, ITIH4, A2M; A1AT, SAA, ApoE, ITIH4, A2M; A1AT, CRP, ApoE, ITIH4, A2M; C1-inh, SAA, CRP, ApoE, ITIH4; C1-inh, SAA, CRP, ApoE, A2M; C1-inh, SAA, CRP, ITIH4, A2M; C1-inh, SAA, ApoE, ITIH4, A2M; C1-inh, CRP, ApoE, ITIH4, A2M; SAA, CRP, ApoE, ITIH4, A2M; ; ; $1^{st}$ 3 plus:: A1AT, C1-inh; A1AT, SAA; A1AT, CRP; A1AT, ApoE; A1AT, ITIH4; A1AT, A2M; C1-inh, SAA; C1-inh, CRP; C1-inh, ApoE; C1-inh, ITIH4; C1-inh, A2M; SAA, CRP; SAA, ApoE; SAA, ITIH4; SAA, A2M; CRP, ApoE; CRP, ITIH4; CRP, A2M; ApoE, ITIH4; ApoE, A2M; ITIH4, A2M; A1AT, C1-inh, SAA; A1AT, C1-inh, CRP; A1AT, C1-inh, ApoE; A1AT, C1-inh, ITIH4; A1AT, C1-inh, A2M; A1AT, SAA, CRP; A1AT, SAA, ApoE; A1AT, SAA, ITIH4; A1AT, SAA, A2M; A1AT, CRP, ApoE; A1AT, CRP, ITIH4; A1AT, CRP, A2M; A1AT, ApoE, ITIH4; A1AT, ApoE, A2M; A1AT, ITIH4, A2M; C1-inh, SAA, CRP; C1-inh, SAA, ApoE; C1-inh, SAA, ITIH4; C1-inh, SAA, A2M; C1-inh, CRP, ApoE; C1-inh, CRP, ITIH4; C1-inh, CRP, A2M; C1-inh, ApoE, ITIH4; C1-inh, ApoE, A2M; C1-inh, ITIH4, A2M; SAA, CRP, ApoE; SAA, CRP, ITIH4; SAA, CRP, A2M; SAA, ApoE, ITIH4; SAA, ApoE, A2M; SAA, ITIH4, A2M; CRP, ApoE, ITIH4; CRP, ApoE, A2M; CRP, ITIH4, A2M; ApoE, ITIH4, A2M; A1AT, C1-inh, SAA, CRP; A1AT, C1-inh, SAA, ApoE; A1AT, C1-inh, SAA, ITIH4; A1AT, C1-inh, SAA, A2M; A1AT, C1-inh, CRP, ApoE; A1AT, C1-inh, CRP, ITIH4; A1AT, C1-inh, CRP, A2M; A1AT, C1-inh, ApoE, ITIH4; A1AT, C1-inh, ApoE, A2M; A1AT, C1-inh, ITIH4, A2M; A1AT, SAA, CRP, ApoE; A1AT, SAA, CRP, ITIH4; A1AT, SAA, CRP, A2M; A1AT, SAA, ApoE, ITIH4; A1AT, SAA, ApoE, A2M; A1AT, SAA, ITIH4, A2M; A1AT, CRP, ApoE, ITIH4; A1AT, CRP, ApoE, A2M; A1AT, CRP, ITIH4, A2M; A1AT, ApoE, ITIH4, A2M; C1-inh, SAA, CRP, ApoE; C1-inh, SAA, CRP, ITIH4; C1-inh, SAA, CRP, A2M; C1-inh, SAA, ApoE, ITIH4; C1-inh, SAA, ApoE, A2M; C1-inh, SAA, ITIH4, A2M; C1-inh, CRP, ApoE, ITIH4; C1-inh, CRP, ApoE, A2M; C1-inh, CRP, ITIH4, A2M; C1-inh, ApoE, ITIH4, A2M; SAA, CRP, ApoE, ITIH4; SAA, CRP, ApoE, A2M; SAA, CRP, ITIH4, A2M; SAA, ApoE, ITIH4, A2M; CRP, ApoE, ITIH4, A2M; A1AT, C1-inh, SAA, CRP, ApoE; A1AT, C1-inh, SAA, CRP, ITIH4; A1AT, C1-inh, SAA, CRP, A2M; A1AT, C1-inh, SAA, ApoE, ITIH4; A1AT, C1-inh, SAA, ApoE, A2M; A1AT, C1-inh, SAA, ITIH4, A2M; A1AT, C1-inh, CRP, ApoE, ITIH4; A1AT, C1-inh, CRP, ApoE, A2M; A1AT, C1-inh, CRP, ITIH4, A2M; A1AT, C1-inh, ApoE, ITIH4, A2M; A1AT, SAA, CRP, ApoE, ITIH4; A1AT, SAA, CRP, ApoE, A2M; A1AT, SAA, CRP, ITIH4, A2M; A1AT, SAA, ApoE, ITIH4, A2M; A1AT, CRP, ApoE, ITIH4, A2M; C1-inh, SAA, CRP, ApoE, ITIH4; C1-inh, SAA, CRP, ApoE, A2M; C1-inh, SAA, CRP, ITIH4, A2M; C1-inh, SAA, ApoE, ITIH4, A2M; C1-inh, CRP, ApoE, ITIH4, A2M; SAA, CRP, ApoE, ITIH4, A2M.

Examples of markers for which an increase relative to control is indicative of rejection include C4A, CRP, SAA, C1-inh, A1AT, and ApoE. Markers for which a decrease relative to control is indicative of rejection include AACT, ApoA1, ITIH4, and A2M.

In one embodiment, the measuring comprises chromatography or spectrometry. The chromatography can be gas or liquid chromatography. The spectrometry can be mass spectrometry. Other known methods of marker detection are also contemplated, and may be selected based on the characteristics of the individual marker of interest. Examples of other assays that can be employed include immunoassay and electrochemical detection. Measures of test samples can be compared directly to controls, such as comparing the amount of the marker present in the test sample to the amount of the marker in a control sample or to a known normal level of the marker. Alternatively, in some embodiments, the marker amount is compared to a baseline amount for the same subject.

The following patent documents pertain to the molecular diagnosis of transplant rejection: U.S. Pat. No. 7,666,596, US 2009/0304705; U.S. Pat. Nos. 7,691,569; 7,645,575; WO 2009/101083; WO 2009/045104; US 2009/0022730; WO 2007/104537; WO 2008/027428; US 2008/0038746; WO 2007/138011; WO 2007/121922; US 2007/0202085; U.S. Pat. No. 7,235,358; US 2007/0037166; US 2006/0088836; U.S. Pat. No. 7,026,121; WO 2004/042346; U.S. Pat. No. 7,192,716; US 2003/0104371; and WO 01/81916. The following patent publications relate to genotypic and phenotypic tests for transplant rejection: US20077235358; WO2006029184; US20070082356; EP000253514; EP000953220; US2004000584728; WO2005077980; US2004000557234; WO02075306; US2006000641625; and US20050152893.

Kits

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. The probes, antibodies and other reagents of the kit may be provided in any suitable form, including frozen, lyophilized, or in a pharmaceutically acceptable buffer such as TBS or PBS. The kit may also include other reagents required for utilization of the reagents in vitro or in vivo such as buffers (i.e., TBS, PBS), blocking agents (solutions including nonfat dry milk, normal sera, Tween-20 Detergent, BSA, or casein), and/or detection reagents (i.e., goat anti-mouse IgG biotin, streptavidin-HRP conjugates, allophycocyanin, B-phycoerythrin, R-phycoerythrin, peroxidase, fluors (i.e., DyLight, Cy3, Cy5, FITC, HiLyte Fluor 555, HiLyte Fluor 647), and/or staining kits (i.e., ABC Staining Kit, Pierce)). The kits may also include other reagents and/or instructions for using antibodies, probes, and other reagents in commonly utilized assays described above such as, for example, liquid or gas chromatography, spectrometry, electrochemical assay, flow cytometric analysis, ELISA, immunoblotting (i.e., western blot), immunocytochemistry, immunohistochemistry.

In one embodiment, the kit provides the reagent in purified form. In another embodiment, the reagents are immunoreagents that are provided in biotinylated form either alone or along with an avidin-conjugated detection reagent (i.e., antibody). In another embodiment, the kit includes a fluorescently labeled immunoreagent which may be used to directly detect antigen. Buffers and the like required for using any of these systems are well-known in the art and may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific application, and can also indicate directions for use, such as those described above. Directions and or other information can also be included on an insert which is included with the kit.

The invention additionally provides a kit comprising antibodies that specifically bind the 5 kDa fragment of C4A, ApoA1, AACT, and, optionally, one or more additional markers listed in Table 1. In one embodiment, the kit comprises reagents that bind C4A (or a 5 kDa fragment thereof) and ApoA1 (or the fragment thereof at amino acids 148-183) and/or AACT (or the fragment thereof at amino acids 385-422), In one embodiment, the kit comprises reagents that specifically bind the 5191 Da fragment of AACT and ApoA1. In one embodiment, the kit further comprises a solid support onto which the antibodies are immobilized. Examples of a solid support include, but are not limited to, a microtiter plate, beads, a membrane or other support known to those skilled in the art. In one embodiment, the antibodies are immobilized via binding to antigen that is immobilized to the solid support. In one embodiment, the antibodies are immobilized via binding to a bead or particle such as luminex. In one embodiment, the kit further comprises a chromogenic substrate.

Another illustrative embodiment of the invention is an ELISA kit to screen for a plasma molecular profile in a patient that is associated with acute cellular renal allograft rejection by detecting α-1 anti-chymotrypsin and/or Apo A1 and/or the 5191 peptide disclosed herein and/or complement C1 inhibitor in plasma or serum, the kit comprising: (a) a microtiter plate coated with polyclonal or monoclonal antibodies specific to α-1 anti-chymotrypsin and/or Apo A1 and/or the 5191 peptide disclosed herein and/or complement C1 inhibitor; (b) polyclonal or monoclonal antibody-alkaline phosphatase conjugates reactive with α-1 anti-chymotrypsin and/or Apo A1 and/or the 5191 peptide disclosed herein and/or complement C1 inhibitor; (c) p-nitrophenyl-phosphate; and (d) α-1 anti-chymotrypsin and/or Apo A1 and/or the 5191 peptide disclosed herein and/or complement C1 inhibitor as an antigen standard.

Another illustrative embodiment of the invention is an ELISA kit to screen for a plasma molecular profile in a patient that is associated with acute cellular renal allograft rejection by detecting α-1 anti-chymotrypsin and/or Apo A1 and/or C4A and/or complement C1 inhibitor in plasma or serum, the kit comprising: (a) a microtiter plate coated with polyclonal or monoclonal antibodies specific to α-1 antichymotrypsin and/or Apo A1 and/or C4A and/or complement C1 inhibitor; (b) polyclonal or monoclonal antibody-alkaline phosphatase conjugates reactive with α-1 antichymotrypsin and/or Apo A1 and/or C4A and/or complement C1 inhibitor; (c) p-nitrophenyl-phosphate; and (d) α-1 anti-chymotrypsin and/or Apo A1 and/or C4A and/or complement C1 inhibitor as an antigen standard.

Another illustrative embodiment of the invention is a Luminex kit to screen in plasma, serum and\or biological fluid for a molecular profile in a patient that is associated with solid organ allograft rejection by detecting α-1 antichymotrypsin and/or Apo A1 and/or C4A and/or complement C1 inhibitor and/or proteins described in Table 1, the kit comprising: (a) a microbead array coated with polyclonal or monoclonal antibodies specific to α-1 anti-chymotrypsin and/or Apo A1 and/or C4A and/or complement C1 inhibitor and/or other proteins listed in Table 1; (b) polyclonal or monoclonal antibody fluorescent dye conjugates reactive with α-1 anti-chymotrypsin and/or Apo A1 and/or C4A and/or complement C1 inhibitor and/or other proteins listed in Table 1; (c) and α-1 anti-chymotrypsin and/or Apo A1 and/or C4A and/or complement C1 inhibitor or other protein in Table 1 as an antigen standard.

EXAMPLES

The following examples are presented to illustrate the present invention and to assist one of ordinary skill in making and using the same. The examples are not intended in any way to otherwise limit the scope of the invention.

Example 1

Apolipoprotein A1 and C-Terminal Fragment of α-1 Antichymotrypsin are Plasma Biomarkers Associated with Acute Renal Allograft Rejection This example demonstrates, using a case-control approach and SELDI-TOF-MS, the identification of plasma proteins associated with renal allograft rejection. From each rejection patient, two plasma samples (one near the biopsy date and the other at a time post-biopsy) were compared. Biopsy confirmed non-rejection patients were further analyzed as controls. Antibody-based quantitative ELISA was performed to validate candidate biomarker apolipoprotein A1 (Apo A1) in a subset of the original and a second cohort of biopsy confirmed rejection (n=40) and non-rejection (n=70) patients. Twenty-two proteins/peptides showed significant differences between rejection and post-rejection samples. Peptides 5191 Da and 4467 Da detected rejection with 100% sensitivity and 94% specificity. The 4467 Da peptide was identified as the C-terminal fragment of α-1 anti-chymotrypsin and a 28 kDa protein was determined as Apo A1. Both protein levels were significantly lower at rejection compared to post-rejection. Protein levels of non-rejection patients were similar to the post-rejection samples. Apo A1 ELISA results showed significantly lower Apo A1 levels (p=0.001 for the original and p=4.14E-11 for the second cohort) at the time of rejection compared to non-rejection which coincides with the SELDI findings. Together α-1 antichymotrypsin, Apo A1, and the 5191 Da peptide (a fragment of C4A) provide a plasma molecular profile, and this is associated with acute cellular renal allograft rejection.

Methods

Study Design and Patient Population. Renal transplant patients were enrolled in the University of California Los Angeles Institutional Review Board-approved immune monitoring study by written consent. Sixteen renal transplant recipients contributed 34 blood specimens associated with 17 "independent" episodes of biopsy-confirmed ACR. One recipient had two rejection episodes far enough apart (4 months), and the intermediate serum creatinine was normal, so we considered the second rejection an independent event. Patients with biopsy-proven nonrejection were also selected (n=48). All biopsies were performed for cause and taken after a serum creatinine rise or delayed graft function. Rejection biopsies occurred within the first 100 days post-transplant with the exception of one which occurred at 656 days (median=27 days posttransplant). Banff classification was used to score acute rejection (35, 36). Two biopsies with ACR also showed evidence of AMR and were C4d positive. The rejection patients were studied at two time points: rejection specimen (group A) were selected at a time point closest to the positive biopsy date (median=−1 day, range: −16 to +8 days); and postrejection samples (group B) were selected closest to 14 days after biopsy date (median=28 days, range: 14-180 days). Twelve of 17 rejection samples (group A) were collected within 8 days before biopsy, and 5 of 17 were obtained within 8 days after the biopsy. For the postrejection samples (group B), 16 of 17 were collected within 60 days after the biopsy, and 1 of 17 was collected at 180 days after the biopsy. The nonrejection plasma samples (defined as controls, group C) were selected at one time point closest to the negative biopsy (median=1 day, range: −35 to +44 days). Table 2 illustrates the demographics of the study population and shows no significant differences with respect to age, gender, race, transplant number, or degree of human leukocyte antigen mismatch. The percentage of deceased and living donors was similar to U.S. Organ Procurement Transplant Network national data.

TABLE 2

Demographic characteristics of patients

| Parameters | Rejection patients (n = 16) | Non-rejectors (n = 48) | P[a] |
|---|---|---|---|
| Age (yr: mean ± SD) | 48.7 ± 12.2 | 49.5 ± 13.9 | 0.84 |
| Gender (male/female) | 14/2 | 32/16 | 0.20 |
| Race | | | 0.74[b] |
| Asian | 19% | 5% | |
| Black | 25% | 20% | |
| White | 44% | 54% | |
| Other | 12% | 21% | |
| Regraft | | | 0.74 |
| First allograft | 81% | 76% | |
| Regraft | 19% | 24% | |
| Multiorgan transplants | | | 0.16 |
| +Pancreas | 11% | 2% | |
| +Liver | 0% | 2% | |
| HLA mismatch (mean ± SD) | 2.7 ± 0.7 | 2.2 ± 1.3 | 0.15 |
| Type of donor | | | 0.21 |
| Deceased | 56% | 74% | |
| Living | 44% | 26% | |
| Induction | | | 0.74[c] |
| Anti-IL2Rα | 74% | 72% | |
| ATG | 22% | 21% | |
| Combined | 4% | 7% | |
| Time of blood draw relative to biopsy (days: median/range) | | | 0.37 |

TABLE 2-continued

Demographic characteristics of patients

| Parameters | Rejection patients (n = 16) | Non-rejectors (n = 48) | P[a] |
|---|---|---|---|
| Rejection sample | −1/−16 to 8 | | |
| Postrejection sample | 28/14 to 147 | | |
| Nonrejection sample | | 1/−35 to 44 | |

[a]P values for categorical variables from Fisher exact test, and P values for continuous variables from t test.
[b]Race (black vs. other).
[c]Induction (ATG vs. any anti-IL2Rα).
ATG, antithymoglobulin; IL2Rα, interleukin-2 receptor alpha chain; SD, standard deviation; HLA, human leukocyte antigen.

A second cohort of recipients with biopsy-proven renal allograft rejection (n=27) were selected, and again two plasma samples were studied (rejection and postrejection time points). All biopsies were performed for cause and taken after a serum creatinine rise or delayed graft function. Two of the ACR positive biopsies also had evidence of AMR, whereas four of the biopsies had evidence of only AMR. Rejection specimens (n=27) were selected at a time point within −7 days of the biopsy (median=−1 day, range=−7 to 0 days). The average rejection episode was 122 days after transplantation. Twenty of the 27 biopsies were within the first 3 months, 5 of 27 were within the first 9 months, and 2 of 27 were greater than 1 year. Postrejection samples were selected more than 8 days after the biopsy (median=32 days, range=8-573 days). For the postrejection samples, 20 of 27 were collected within 3 months after the biopsy, 3 of 27 were within 6 months, 1 of 27 was collected at 9 months, and 3 of 27 were collected 1 year after the biopsy. In addition, a cohort of 51 biopsy-proven nonrejection samples were selected at a time closest to the negative biopsy (median=8 days, range=−22 to 581 days). For the biopsy-proven nonrejection samples, 38 of 51 were collected within 3 months after the biopsy, 5 of 51 were within 6 months, 4 of 51 were collected within 9 months after the biopsy, and 4 of 51 were collected after 1 year. All biopsies from this group of nonrejectors were performed for cause and taken after a serum creatinine rise or delayed graft function.

For both cohorts, maintenance immunosuppression included a calcineurin inhibitor (tacrolimus or cyclosporine), an antiproliferative agent (mycophenolate mofetil or sirolimus), and prednisone. In some cases without evidence of pretransplant sensitization, steroids were withdrawn.

Plasma Albumin and Immunoglobulin-G Depletion and Anion Exchange Fractionation

Blood samples were collected in BD Vacutainer ACD solution A tubes (Becton, Dickinson and Company, Franklin Lakes, N.J.). Plasma was separated and stored. Antibody spin columns (Qproteome, Qiagen, Valencia, Calif.) were used to deplete human serum albumin and immunoglobulin-G. Complete Mini (ethylenediaminetetraacetic acid) Protease Inhibitor (Roche, Palo Alto, Calif.) was added. Acro-Prep Mustang Q (hydrophilic polyethersulfone membrane) Anion Exchange Resin 96-well plates (Pall, East Hills, N.Y.) were used to separate the depleted plasma into the pH 9, pH 6, and pH 4 fractions.

ProteinChip Array preparation

ProteinChip arrays (CM10 and Q10) were preequilibrated for binding, pH fractions were bound to the arrays and analyzed in triplicate. Six pooled human serum (Sigma, St. Louis, Mo.) samples were used as internal controls on each array set. After sample array processing, matrix was applied: either saturated sinapinic acid (SPA, LaserBio Labs, Sophia-Antipolis, France) or 20% saturated alpha-cyano-4-hydroxy cinnamic acid (CHCA, LaserBio Labs). A Biomek 2000 liquid handling robot (Beckman, Fullerton, Calif.) was used for matrix spotting.

Mass Spectrum Data Analysis

A ProteinChip Biology System (PBS IIc) mass spectrometer using Ciphergen ProteinChip Software 3.2 was calibrated in the high mass range before reading the SPA-spotted arrays (laser energies of 150 and 170). A peptide mixture was used for calibration of the CHCA-spotted arrays (laser energies of 120 and 135). Mass spectrum from each spot was an average of 240 laser shots. All spectra were preliminarily analyzed in CiphergenExpress Client Software 3.0 to create clusters by Expression Difference Mapping analysis. A cluster is a group of peaks with the same mass/charge (m/z) ratio and treated as the same protein or peptide across multiple spectra. Peak intensities from each spectrum were used to measure relative protein/peptide amounts. Total ion current was used to normalize the signals. The reproducibility of peak heights was similar to what was previously published (37), showing a CV of 15% to 30%.

Protein Identification

MALDI-TOF-MS was performed with a prOTOF 2000 orthoganol-TOF mass spectrometer (Perkin Elmer, San Jose, Calif.). The high-performance liquid chromatography system was Prominence 2000 (Shimadzu Scientific Instruments, Columbia, Md.). All protocol and reagents were in accordance with manufacturer's suggestions.

4467 Da Peptide

Q fractions with this peptide were loaded on a reverse phase C8 column (Axxiom, Moorpark, Calif.). The C8 fractions were subjected to collision-induced dissociation MS/MS fragmentation in a Thermo-Finnigan LTQ-FT electrospray mass spectrometer (Waltham, Mass.). The MS/MS data were searched by NCBI Blast. Immunoprecipitation was performed using a polyclonal antibody against α-1-antichymotrypsin (Lab Vision Corporation, Fremont, Calif.) followed by MALDI analysis.

28 kDa Protein

Pooled samples fractions with high levels of the protein were separated by sodium dodecyl sulfate-PAGE. The gel was stained using the ProteoSilver Plus kit (Sigma). Bands near 28 kDa were excised, and in-gel tryptic digestion was performed. Peptides were analyzed by MALDI. Intact tryptic masses were searched in MASCOT with online protein fragment database searching. Immunoprecipitation was done using a monoclonal antibody against human Apo A1 (R&D Systems, Minneapolis, Minn.) followed by MALDI analysis.

Statistical Analyses

Nonparametric (binomial) and parametric (mixed effects and linear regression) models were used to identify significant peaks. Two-sided P values less than 0.05 were considered significant, and Bonferroni correction was used as needed. CART analysis was conducted to select a subset of candidate biomarkers and determine their ability to correctly classify rejection. Adjusted intensities of the selected protein/peptide peaks were used as the predictor variables in CART training. The R software package (version 3.1, at r-project.org) was used for statistical computations. Traditional logistic regression analysis was performed, and ROC plots were generated using STATA data analysis and statistical software. Cut points were selected by the maximum correctly classified. Details of the statistical analyses are presented in the Supplemental material (see Supplemental Digital Content 1, links.lww.com/TP/A465; published with the online version of this material as Ziegler, M. E., et al., 2011, Transplantation 92(4):10.1097).

ELISA for Quantitation of Plasma Apo A1 Levels

Total Human Apolipoprotein A1 ELISA Assay (Alerchek, Portland, Me.) was used according to the manufacturer's protocol. Samples were run in duplicate along with a control plasma sample. Analysis was performed on the SpectraMax M2 plate reader with the SoftMax Pro 5.4 software (Molecular Devices, Sunnyvale, Calif.).

Results

Variations in Plasma Protein/Peptide Levels Between Rejection and Postrejection Samples The peak intensity differences across spectra between the rejection and postrejection groups were analyzed. In total, 653 peak clusters were detected, including 235 peaks in the pH 4 fraction, 186 peaks in the pH 6 fraction, and 232 peaks in the pH 9 fraction.

The peak intensities of rejection and postrejection samples from the same patient were analyzed using a binomial model. Eighty-one peak intensities (see Table S1A, Supplemental Digital Content 1, links.lww.com/TP/A465) were significantly increased, whereas 63 peaks (see Table S1B, Supplemental Digital Content 1) were significantly decreased in the rejection samples. After Bonferroni correction for the total number of peaks in each condition, 24 peaks (Table S2, Supplemental Digital Content 1, at links.lww-.com/TP/A465) were significantly different between rejection and postrejection samples by the linear mixed model. Twenty-two significant protein peaks were detected by both the binomial model and the linear mixed model (Table 3).

TABLE 3

Significant peaks found by both the linear mixed model and binomial model

|   | Condition[a] | Protein peak m/z (Da) | P for mixed model | P for binomial model | Protein intensity ratio[a] (>1.5) |
|---|---|---|---|---|---|
| 1 | 4CL | 4467 | 3.06E-04 | 0.004 | B/A |
| 2 |  | 4125 | 1.35E-04 | 0.011 | A/B |
| 3 |  | 5191 | 1.15E-11 | 0.000 | A/B |
| 4 | 4SH | 50,835 | 5.04E-06 | 0.003 | A/B |
| 5 |  | 143,718 | 3.62E-05 | 0.001 | B/A |
| 6 | 6CL | 4564 | 4.41E-05 | 0.030 | A/B |
| 7 |  | 4933 | 1.80E-04 | 0.030 | A/B |
| 8 |  | 5191 | 1.10E-06 | 0.002 | A/B |
| 9 | 6SH | 59,256 | 2.24E-04 | 0.025 | B/A |
| 10 |  | 60,334 | 3.72E-04 | 0.025 | B/A |
| 11 |  | 63,615 | 5.74E-04 | 0.000 | B/A |
| 12 |  | 123,329 | 2.10E-04 | 0.025 | B/A |
| 13 | 9CL | 5051 | 3.29E-05 | 0.001 | A/B |
| 14 |  | 5083 | 6.40E-05 | 0.020 | A/B |
| 15 |  | 5190 | 8.58E-07 | 0.020 | A/B |
| 16 |  | 5265 | 1.21E-05 | 0.001 | A/B |
| 17 | 9SH | 28,186 | 2.18E-04 | 0.002 | B/A |
| 18 |  | 28,336 | 1.42E-04 | 0.007 | B/A |
| 19 |  | 28,574 | 3.00E-04 | 0.007 | B/A |
| 20 |  | 29,134 | 1.40E-04 | 0.026 | B/A |
| 21 |  | 109,796 | 1.05E-04 | 0.007 | B/A |
| 22 |  | 188,758 | 2.59E-04 | 0.026 | B/A |

[a] Under "Condition," the number refers to the pH fraction. The "Ratio" indicates whether the protein intensity is higher in rejection (A) or postrejection (B) patients.
C, alpha-cyano-4-hydroxy cinnamic acid; S, sinapinic acid; L, low laser energy; H, high laser energy; m/z, mass to charge ratio.

The 17 independent rejection events were applied to a Classification and Regression Tree (CART) analysis and produced a combination of two peaks (4467 Da and 5191 Da) (FIG. 1A), which best differentiate rejection from postrejection samples. All the rejection samples were correctly detected, whereas only one postrejection sample was incorrectly detected; showing 100% sensitivity and 94% specificity. The intensity of the 5191 Da peak was significantly increased during rejection (P<0.001), whereas the 4467 Da peak was significantly decreased during rejection (P<0.004) (FIG. 1B). The ROC plots produced cut points, which were similar to those found by CART analysis.

The peak intensities of these two proteins were compared with the nonrejection group (group C) (FIG. 1B). There was no significant difference in 5191 Da peak intensity between groups B and C (P=0.33). However, in rejection (group A), the 5191 Da peak was elevated over nonrejection (group C) (P<0.001). The 4467 Da peak intensity was lower during rejection (group A) (P<0.001) compared with nonrejection (group C), and nonrejection (group C) was only slightly higher than the postrejection samples (group B, P=0.04).

Although the levels of the 5191 DA and 4467 DA protein peaks were significantly associated with diagnosis of rejection, their intensities did not appear to discriminate among Banff grades of rejection. Because of the limited numbers, rejections were classified as either mild (≤Banff 1A, n=10) or severe (≥Banff 1B, n=7). The two groups individually showed the same intensity patterns (versus nonrejection) as listed earlier for the combined cases of rejection (data not shown).

Of the plasma samples used for protein profiling, blood sample serum creatinine levels were available in 16 of 17 rejection samples and 19 of 48 controls. There was no significant difference in serum creatinine levels between postrejection and samples collected during rejection. Although the creatinine levels in the postrejection samples (median=1.9) were in fact lower in all patients compared with the time of rejection (median=2.2), this difference was not statistically significant. Creatinine recovery can be slower due to a number of factors including type of rejection, the rejection therapy, and the donor condition.

Identification of Biomarker Candidates

The 4467 Da peptide was detected in the pH 4 fraction, and further purification revealed a cluster of peaks (FIG. 2A) with mass differences matching the monoisotopic masses of valine, leucine, alanine, and serine giving a terminal sequence of SALV (S, serine; A, alanine; L, leucine; and V, valine), which corresponds to the C-terminal fragment of human α-1-antichymotrypsin (AACT). High-resolution MALDI analysis of immunoprecipitated plasma peptides confirmed the identity as AACT (FIG. 2B).

Figure 2C:
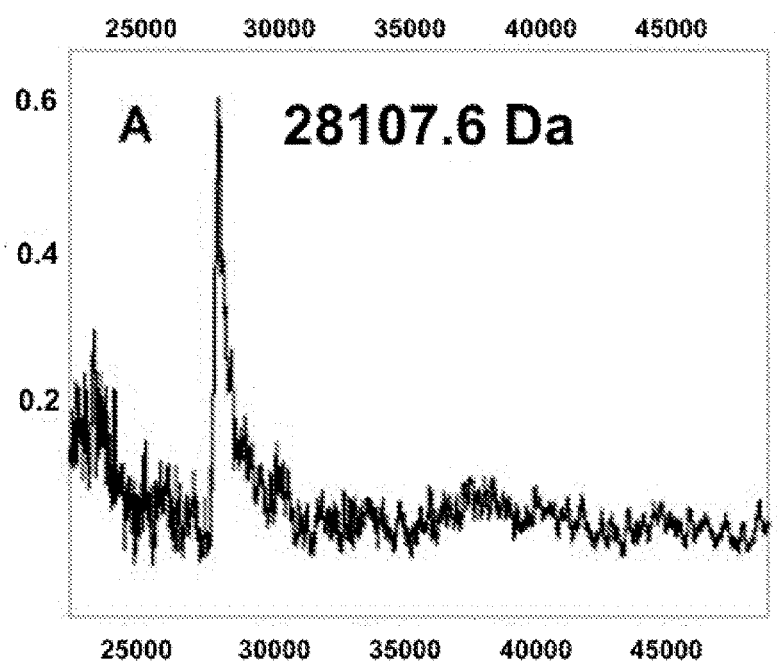
Figure 2D:
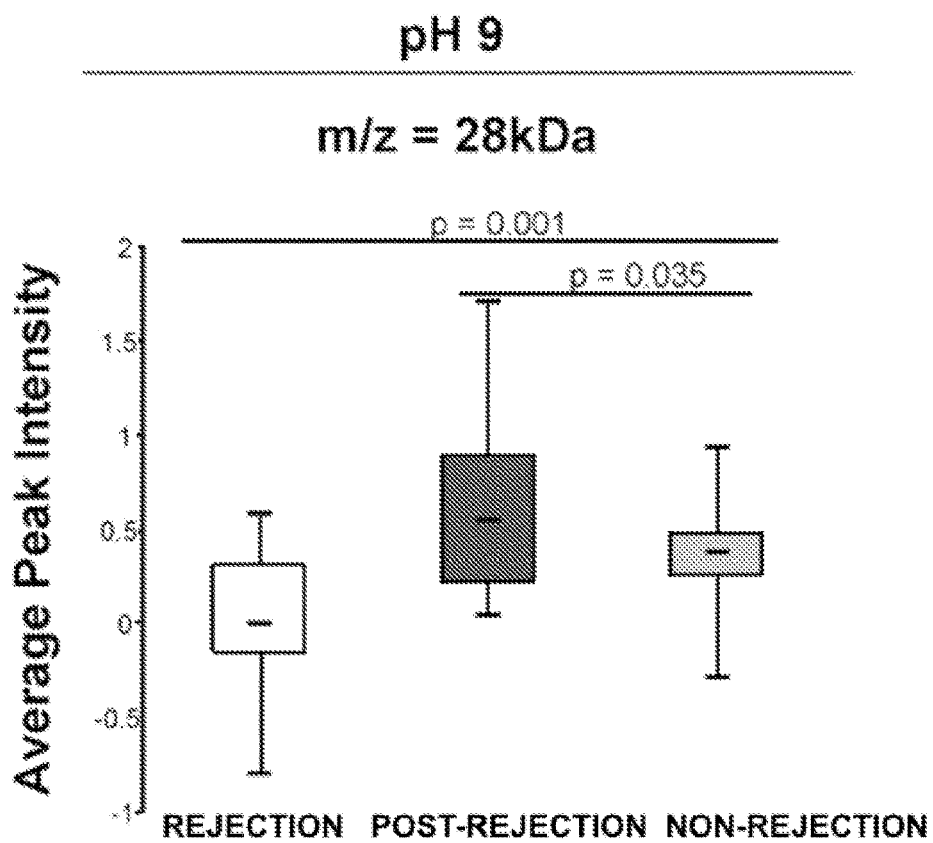

To further develop a profile associated with renal allograft rejection, a cluster of peaks at ~28 kDa found among the list of 22 significant proteins was analyzed (Table 3). Separation of the 28 kDa peaks by sodium dodecyl sulfate-PAGE followed by in-gel tryptic digestion produced peptides that were analyzed by MALDI-TOF-MS and searched on MASCOT to identify the protein as Apo A1. Immunoprecipitation using a monoclonal antibody confirmed the identity (FIG. 2C). The Apo A1 peak intensity was significantly higher in postrejection compared with the rejection and nonrejection patients and were more similar to the postrejection (P=0.035) than the rejection samples (P=0.001) (FIG. 2D). Although Apo A1 protein levels were significantly associated with diagnosis of acute rejection, they were not associated with an individual Banff grade of rejection. Logistic regression and CART analysis of the 4467 Da and the 28 kDa peaks showed that they differentiate rejection from postrejection with 59% sensitivity and 100% specificity.

Validation of Apo A1

Figure 3A:
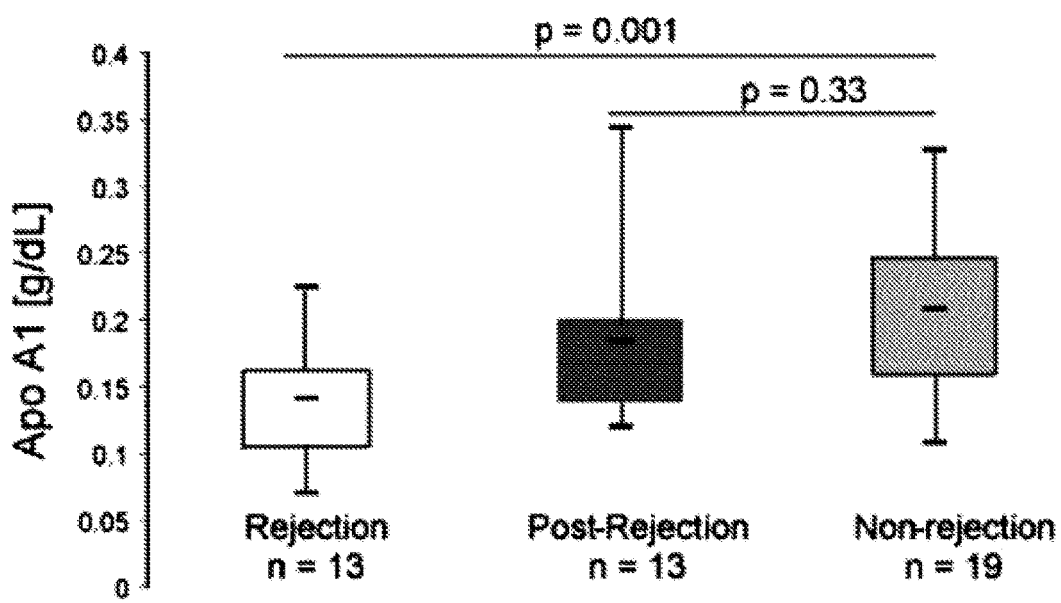
FIGS. 3A-3D: Validation of apolipoprotein A1 (Apo A1) by enzyme-linked immunosorbent assay (ELISA) for association with acute cellular rejection. (3A) Box plots of the ELISA results of plasma samples of a subset of the original cohort. (3B) Box plots of the ELISA results of the plasma samples of the second independent cohort. (3C) Box plots of Apo A1 levels in recipients that had a sample collected within −3 to 0 days before the renal biopsy. Twenty-five rejection and 22 nonrejection samples were compared. The mean Apo A1 levels in nonrejection was 0.22 SD±0.06 and 0.13 SD±0.04 in rejection. The levels of Apo A1 were significantly lower at the time of rejection (P value <0.0001) compared with recipients with biopsy-proven nonrejection. (3D) Line graph indicating the individual Apo A1 results for 14 patients who had plasma samples from all three time periods (prerejection, rejection, and postrejection). (E) ROC analysis comparing the rejection samples to the nonrejection samples from both the original cohort and the second cohort combined showing a cut point of 0.167 mg/dL and 76% sensitivity and 86% specificity.
Figure 3B:
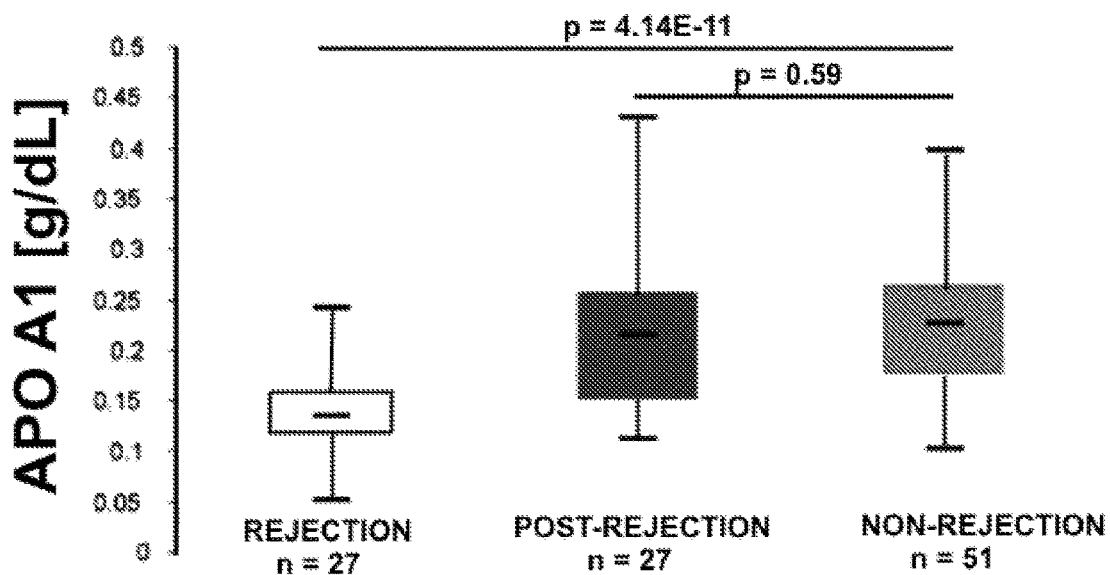

To validate the SELDI results, a quantitative Apo A1 ELISA was performed on a subset of the original rejection/postrejection samples (n=13) and the nonrejection samples (n=19). The pattern of Apo A1 levels measured by ELISA (FIG. 3A) is consistent with the SELDI intensity peak levels (FIG. 2D). To further substantiate these findings, the Apo A1 ELISA was performed on an independent cohort consisting of 27 plasma samples from patients with biopsy-confirmed acute cellular rejection (ACR) with a corresponding postrejection sample and 51 patients with biopsy-proven nonrejection. In the second cohort, Apo A1 levels by ELISA are significantly lower during rejection (mean=0.14±0.04), compared with postrejection (mean=0.22±0.09) and nonrejection samples (mean=0.23±0.07, P=4.14E-11) (FIG. 3B), a finding that is consistent with the original cohort.

Figure 3C:
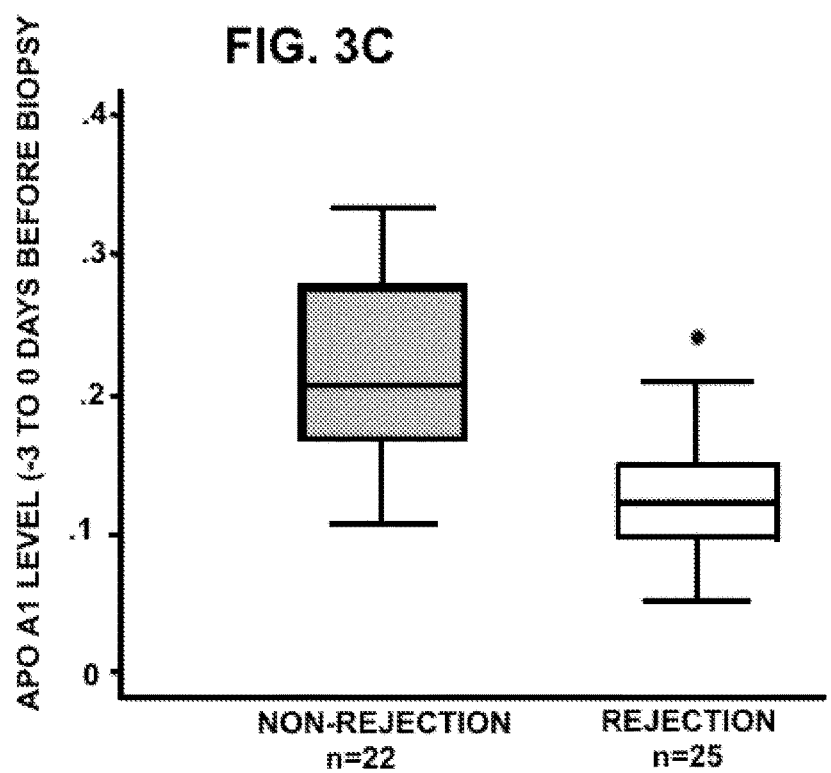

Among both cohorts, samples which were collected within −3 to 0 days before the renal biopsy were examined. Twenty-five rejection and 22 nonrejection samples were compared, and Apo A1 levels were significantly lower at the time of rejection (P value<0.0001) compared with recipients with biopsy-proven nonrejection (FIG. 3C).

Figure 3D:
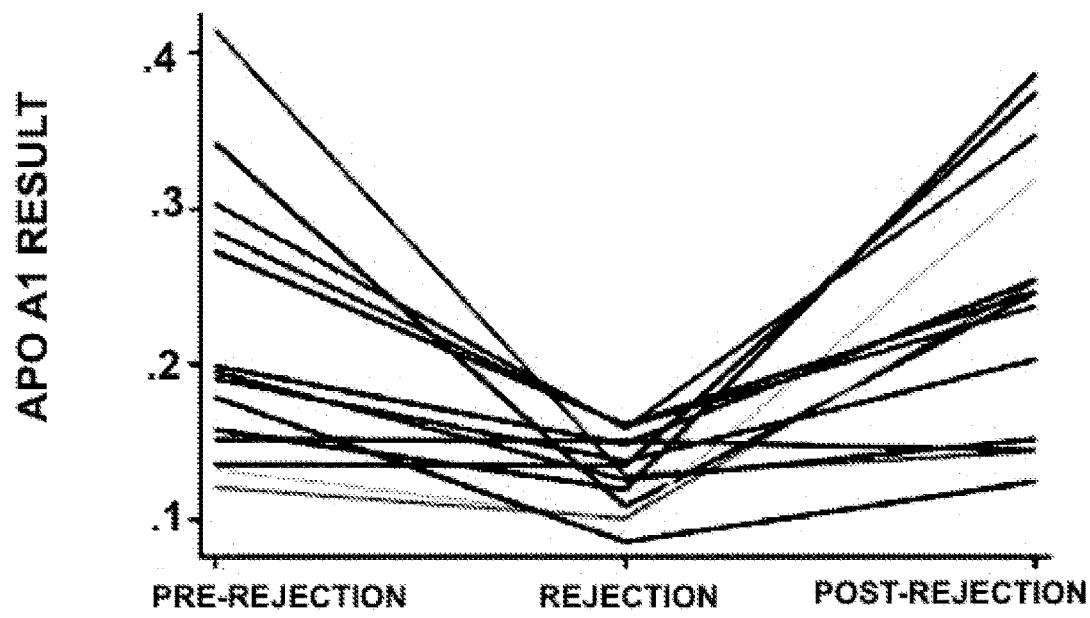

A subset of the new cohort (n=14) also had available a plasma sample collected at a time point before the rejection episode (median=−50 days, range=−180 to −11 days). The prerejection samples demonstrated Apo A1 levels nearly identical to the average levels of the postrejection samples (FIG. 3D).

An ROC analysis was performed using Apo A1 levels of the rejection and nonrejection samples from both the original and second cohort of patients (FIG. 3E). The results show a cut point of 0.167 g/dL provides a sensitivity of 76% and a specificity of 86% correctly detecting 80% of the patients. Twenty-six of the 27 rejection patients had Banff classification data as follows: borderline changes=2, Banff 1A=13, Banff 2A=6, Banff 3 vascular=1, and Banff antibody-mediated rejection (AMR)=4. The patients were grouped into categories based on mild ACR (borderline and Banff 1A=15), severe ACR (Banff 2A and Banff 3 vascular=7), or AMR with no ACR (n=4). The Apo A1 medial level was 0.14 for all three groups indicating that the severity of rejection was not distinguished by the Apo A1 level.

Discussion

Twenty-two peptides/proteins discovered by surface-enhanced laser desorptionionization time-of-flight mass spectrometry were significantly associated with the diagnosis of acute allograft rejection. The identity of two of these proteins, AACT and Apo A1, was elucidated. The C-terminal fragment of AACT is significantly lower during rejection compared with postrejection and nonrejection. A different variation of the AACT fragment (4354 Da) is found at higher levels in urine of patients with acute rejection compared with those with stable transplants (14). Pimenta et al. (17) examined the hydrolysis of AACT by cathepsin D using high-performance liquid chromatography isolation and MADLI and found three peptides: 4354 Da, 4468 Da, and 4625 Da. These cleavage products are identical to the 4467 Da peak identified in plasma and the 4354 Da found in urine based on the sequence data, suggesting that both may be produced by cathepsin D.

O'Riordan et al. (14) examined the levels of total AACT in the kidney by immunohistochemistry and found no difference between rejection and controls and suggested that finding a peptide AACT whose level varied was the result of cleavage after target protease interaction, and therefore, the peptide level variation between patients is a reflection of the activity of the AACT target proteases. We hypothesize that variations in the peptide level may be a result of total AACT being blocked or bound to other substrates for cathepsin D such as cystatin C or kininogen (18). Alternatively, during rejection, total AACT may instead inhibit its primary target, cathepsin G (19), an inflammation-related neutrophil protease, which has been linked to allograft function (20, 21).

The 28 kDa peak was identified as Apo A1. Apo A1 and synthetic peptides, which mimic Apo A1 activity, have strong antiinflammatory and antioxidant properties (22, 23). The Apo A1 mimetic peptide, D-4F, reduces intimal lesions caused by chronic rejection in a mouse model. The mechanism of this effect involves induction of the antioxidant gene heme oxygenase-1 in the graft and/or a direct effect on T-lymphocyte proliferation and effector cytokine production (24).

Apo A1 was validated by ELISA in both the original and an independent cohort. Comparisons of the rejection, postrejection, and nonrejection samples in both cohorts were consistent with the SELDI findings indicating that lower levels of Apo A1 are associated with rejection. The prerejection time point in the independent cohort could not predict the onset of the rejection episode, indicating that the Apo A1 drop is closely associated with the time of rejection. In addition, the Apo A1 ROC analysis of all patients suggests that Apo A1 could potentially be part of a signature used to describe rejection. Apo A1 was also identified as a candidate biomarker in pulmonary arterial hypertension, colorectal cancer, and ovarian cancer (25-27) and more recently was associated with Chagas disease, polycystic ovarian syndrome, and chronic obstructive pulmonary disease (28-30). In all these studies, Apo A1 levels were lower in the disease state compared with nondisease.

Infections can lead to changes in serum lipid profiles, and decreased Apo A1 has been postulated to link infection with chronic inflammation (31). The use of long-term immunosuppressive therapy leaves transplant patients susceptible to infection (32). We examined the 51 nonrejection patients from the second cohort and found five patients with evidence of bacterial infection at the time the plasma sample used for this study was collected. Apo A1 levels were not significantly different in nonrejection patients with infection compared with those without for this small subset of patients. This contributes to the hypothesis that for renal transplant patients, low levels of Apo A1 are associated with the rejection episode, but more studies are necessary to confirm this.

Isolation and identification of the 5191 Da peptide have been hindered due to its low abundance in plasma, its copurification with other more abundant peptides, and the inability to directly fragment it. For unknown reasons, some peptides fragment poorly and yield MS/MS spectra that cannot be deciphered (33, 34). A combination of the 5191 and 4467 Da peaks robustly assessed rejection verses nonrejection, whereas the combination of the 4467 and 28 kDa peaks was not as valuable, thus identification of the 5191 Da peak is important. We are currently exploring alternative methods to better isolate and fragment this peptide for identification.

A limitation of our study design is that the plasma was collected at routine patient visits, which was not always on the same day that the renal biopsy was performed. Also, the clinical parameters of our study population were not uniform with respect to immunosuppression. Furthermore, only two patients in the original cohort had AMR, and therefore, a signature for AMR could not be determined. A majority of patients rejected within the first 100 days, and thus, we were limited to only explore early rejection. In the future, it will be also valuable to explore these markers in patients undergoing late renal allograft rejection. Additionally, we did not find an association between severity of rejection based on Banff classification and Apo A1 levels. It would be of interest to attempt this comparison again in a larger cohort of subjects. Finally, we recognize that to better assess these markers, a prospective study is necessary to determine their true value in the clinical setting. To show the potential of a prospective study, we examined both cohorts of patients and found 25 rejection and 22 nonrejection samples collected −3 to 0 days before the renal biopsy. When we compared the Apo A1 levels between these groups, the rejection levels were significantly lower (P<0.0001), suggesting that a prospective study would likely have differentiated these patients at the time of biopsy.

This study demonstrates that searching for candidate biomarkers of renal allograft rejection in plasma has a promising clinical benefit. At the time point these plasma samples were collected, the candidate biomarkers showed variations that were more informative than serum creatinine level changes. Therefore, future studies should not only interrogate Apo A1 but also other markers for their ability to accurately detect renal allograft rejection. Finally, the two candidate markers identified are antiinflammatory proteins, and their functional characterization should be explored.

1. Li B, et al. N Engl J Med. 2001; 344:947.
2. Clarke W. Ther Drug Monit. 2006; 28:19.
3. Beckingham I J, et al. Br J Urol. 1994; 73:13.
4. Rush D N, et al. Transplantation. 1994; 57:208.
5. Hu S. et al. Proteomics. 2006; 6:6326.
6. Lescuyer P, et al. J Proteome Res. 2007:6:3371.
7. Reddy G, Dalmasso E A. J Biomed Biotechnol. 2003; 2003:237.
8. Albitar M, et al. Cancer. 2006; 106:1587.
9. Clarke W, et al. Ann Surg. 2003; 237:660-4. discussion 664.
10. Schaub S, et al. Kidney Int. 2004; 65:323.
11. O'Riordan E, et al. J Am Soc Nephrol. 2004; 15:3240.
12. Voshol H, et al. J Proteome Res. 2005; 4:1192.
13. Jahnukainen T, et al. J Am Soc Nephrol. 2006; 17:3248.
14. O'Riordan E, et al. Am J Transplant. 2007; 7:930.
15. Ling X B, et al. J Am Soc Nephrol. 2010; 21:646.
16. Freue G V, et al. Mol Cell Proteomics. 2010; 9:1954.
17. Pimenta D C, et al. J Protein Chem. 2000; 19:411.
18. Lenarcic B, et al. FEBS Lett. 1991; 280:211.
19. Zhang S, Janciauskiene S. J Alzheimers Dis. 2002; 4:115.
20. Gibson T L, Cohen P. Growth Horm IGF Res. 1999; 9:241.
21. Koo D D, et al. Am J Pathol. 1998; 153:557.
22. Navab M, et al. Circulation. 2002; 105:290.
23. Navab M, et al. Arterioscler Thromb Vasc Biol. 2005; 25:1325.
24. Hsieh G R, et al. Transplantation. 2007; 84:238.
25. Yuditskaya S, et al. Blood. 2008; 113:1122.
26. Engwegen J Y, et al. World J Gastroenterol. 2006; 12:1536.
27. Kozak K R, et al. Proteomics. 2005; 5:4589.
28. Ndao M. et al. J Clin Microbiol. 2010; 48:1139.
29. Choi D H, et al. J Proteome Res. 2010; 9:4329.
30. Nicholas B L, et al. Am J Respir Crit Care Med. 2010; 181:1049.
31. Burger D, Dayer J M. Autoimmun Rev. 2002; 1:111.
32. Fishman J A, Rubin R H. N Engl J Med. 1998; 338:1741.
33. Shevchenko A. et al. Methods Mol Biol. 2000:146:1.
34. Shevchenko A, et al. Rapid Commun Mass Spectrom. 1997; 11:1015.
35. Racusen L C, et al. Am J Transplant. 2003; 3:708.
36. Racusen L C, et al. Kidney Int. 1999; 55:713.
37. Albrethsen J. Clin Chem. 2007; 53:852.

Example 2

Validation of Apolipoprotein A1 (Apo A1) as a Plasma Biomarker Associated with Acute Renal Allograft Rejection The 28 kDa protein identified in Example 1 as Apo-A1 consistently showed lower levels in patients with biopsy proven renal allograft rejection. Using an enzyme-linked immunosorbent assay (ELISA) and an independent cohort of 27 plasma samples from patients with biopsy proven rejection and 51 patients without rejection, we confirmed the mass spectrometry studies and showed that lower levels are associated with diagnosis of renal allograft rejection.

The aim of the current study was to validate the predictive value of the marker for renal allograft rejection using an independent cohort of 73 renal allograft recipients transplanted at UCLA between 2010 and 2013. 45/71 patients had rejection while 28 patients had biopsy proven non-rejection.

Figure 4:
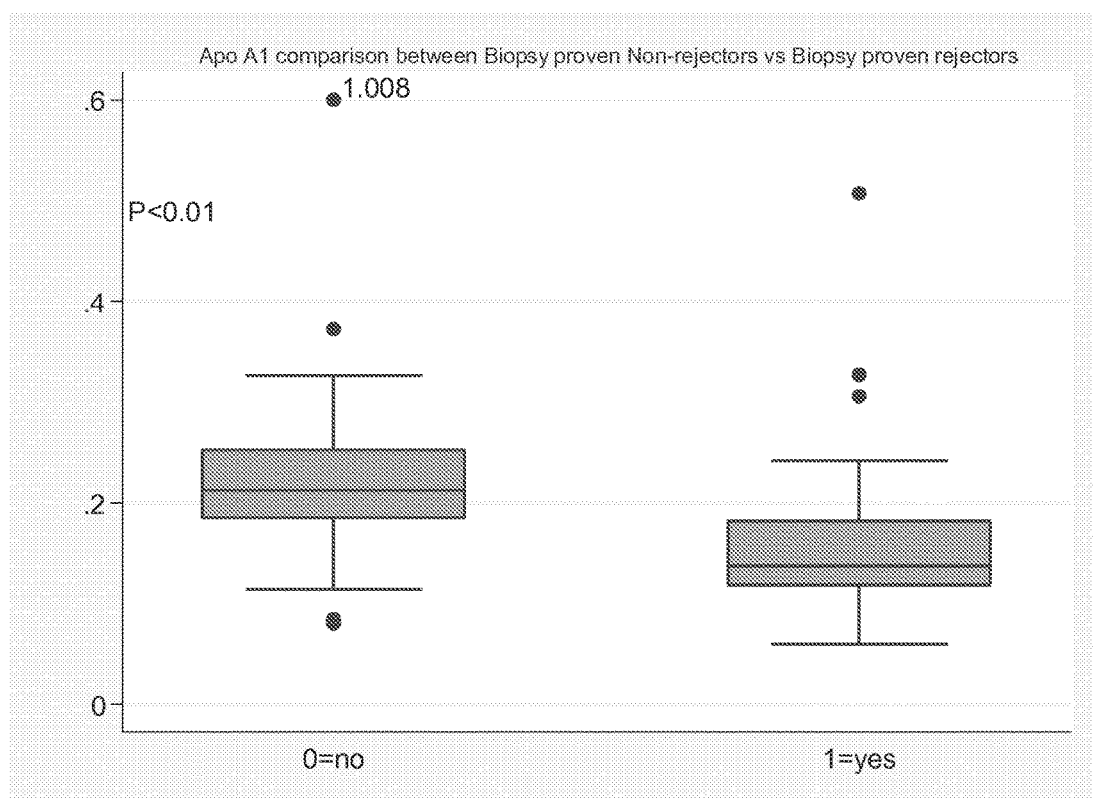
FIG. 4: ApoA1 comparison between biopsy proven non-rejectors versus biopsy proven rejectors, showing that patients diagnosed with renal allograft rejection had significantly lower Apo A1 levels (mean 0.156+/−0.77) compared to non-rejection (mean 0.239+/−0.16) (P<0.0024).
Figure 5:
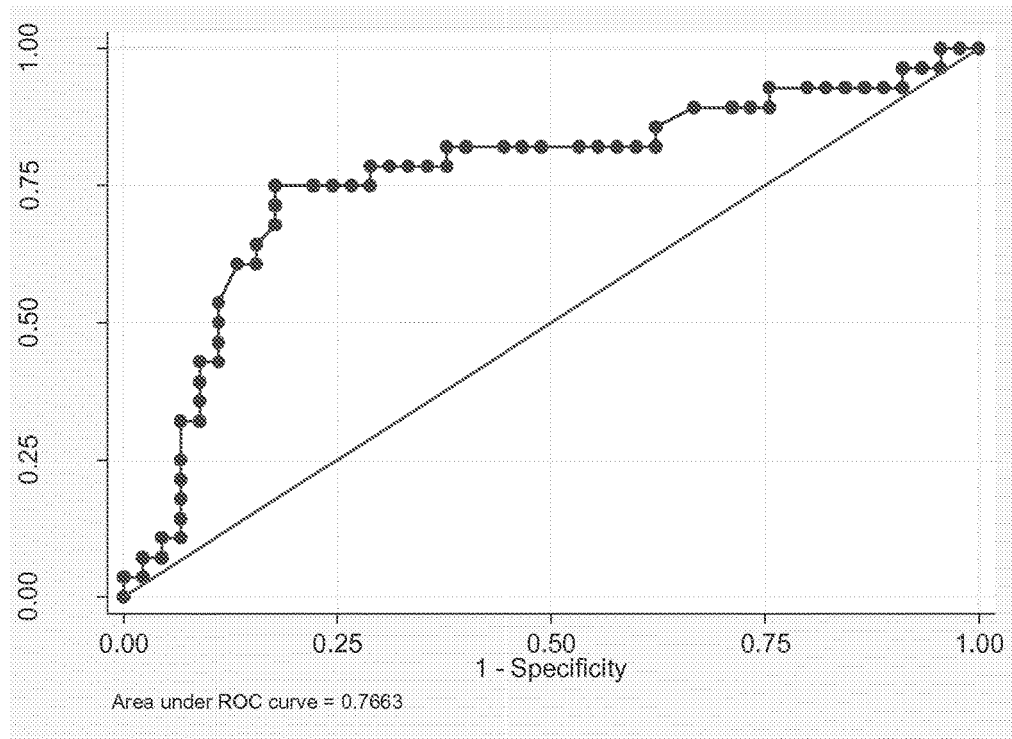
FIG. 5: Sensitivity and specificity of ApoA1 comparison between biopsy proven non-rejectors versus biopsy proven rejectors. Using a cutpoint of 0.195, Apo A1 levels correctly classified patients with rejection 79% of the time with a sensitivity of 75% and specificity of 82%.

Plasma samples from 73 renal recipients were assayed for Apo-A1 protein levels by ELISA. 45 of the patients experienced at least one biopsy proven rejection episode while 28 patients had biopsy proven no-rejection. Plasma samples obtained within 7 days prior or 2 days after diagnosis of rejection were quantitated by ELISA for Apo A1 levels. Renal allograft rejection was diagnosed using Banff criteria. As shown in Table 3 and FIG. 4, patients diagnosed with renal allograft rejection had significantly lower Apo A1 levels (mean 0.156+/−0.77) compared to non-rejection (mean 0.239+/−0.16) (P<0.0024). Using a cutpoint of 0.195, Apo A1 levels correctly classified patients with rejection 79% of the time with a sensitivity of 75% and specificity of 82% (FIG. 5).

TABLE 3

T test for first biopsy per transplant ttest maxb1 if brnk == 1, by (rej)
Two-sample t test with equal variances

| Group | Obs | Mean | Std. Err. | Std. Dev. | [95% Conf. Interval] | |
|---|---|---|---|---|---|---|
| 0 = no | 28 | .2399732 | .0312028 | .1651096 | .1759504 | .303996 |
| 1 = yes | 45 | .1568389 | .0114993 | .0771399 | .1336635 | .1800143 |
| combined | 73 | .188726 | .0145791 | .1245642 | .1596631 | .217789 |
| diff | | .0831343 | .0285355 | | .0262361 | .1400325 |

| diff = mean(0 = no) − mean(1 = yes) | t = 2.9134 |
|---|---|
| Ho: diff = 0 | degrees of freedom = 71 |
| Ha: diff < 0 | Ha: diff != 0 | Ha: diff > 0 |
| Pr(T < t) = 0.9976 | Pr(|T| > |t|) = 0.0048 | Pr(T > t) = 0.0024 |

Conclusion: Significantly lower Apo A1 protein levels are found within a week of diagnosis of renal allograft rejection. This study further supports using Apo A1 as a biomarker of renal allograft rejection and can be used to not only aid in the diagnosis of renal allograft rejection but it may be used to monitor transplant recipients to determine risk of rejection.

Example 3

Validation of Alpha-2-Macroglobulin Using an Antibody-based ELISA Assay

Figure 6:
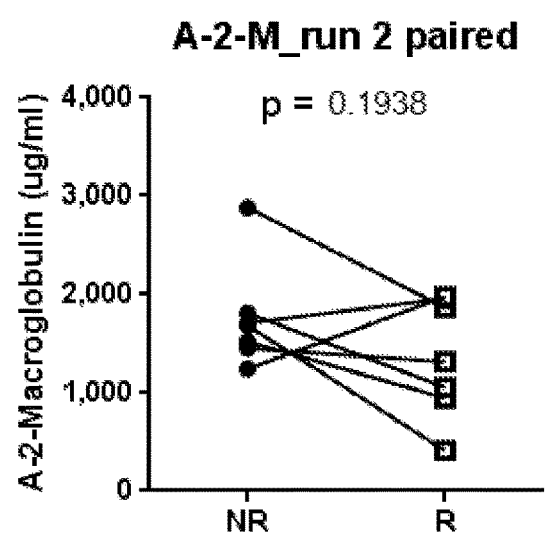
FIG. 6: Validation of Alpha-2-macroglobulin using an antibody-based ELISA.

FIG. 6 presents ELISA data showing the same patter of detection of Alpha-2-macroglobulin as was demonstrated using mass spectrometry. Paired plasma samples were collected at the time of rejection and post-rejection from 7 renal allograft recipients diagnosed with rejection. These are the same paired serum samples that were used in Example 1 above. The data show that the levels of Alpha-2-macroglobulin as detected by ELISA decrease at the time of diagnosis of rejection.

Example 4

Amino Acid Sequences of Biomarkers Identified by Mass Spectrometry

Amino acid sequences of protein fragments identified in Example 1 above were determined as described in the following Table.

TABLE 4

Amino Acid Sequences of
Biomarker Peptides and Proteins

Alpha-1-antitrypsin C-Terminal fragment
(2505 Da, A1AT 397-418; SEQ ID NO: 11)
LMIEQNTKSPLFMGKVVNPTQK Apolipoprotein A1 fragment
(4125 Da, Apo A1 148-183; SEQ ID NO: 5)
AELQEGARQKLHELQEKLSPLGEEMRDRARAHVDAL Plasma protease C1 inhibitor fragment
(4187 Da, C1 inh 445-478; SEQ ID NO: 13)
ARTLLVFEVQQPFLFVLWDQQHKFPVFMGRVYDPRA (+2 Ox)

Alpha-1-antichymotrypsin C-terminal fragment
(4467 Da, AACT 385-422; SEQ ID NO: 8)
ALVETRTIVRFNRPFLMIIVPTDTQNIFFMSKVTNPKQ TABLE 4-continued Amino Acid Sequences of
Biomarker Peptides and Proteins Complement C4 Anaphylatoxin
(5051 Da, C4 alpha 698-742; SEQ ID NO: 3)
TAKRCCQDGVTRLPMMRSCEQRAARVQQPDCREPFLSCCQFAESL Complement C4 Anaphylatoxin
(5191 Da, C4 alpha 702-746; SEQ ID NO: 2)
CCQDGVTRLPMMRSCEQRAARVQQPDCREPFLSCCQFAESLRKKS Serum Amyloid A-4
(11694 Da, SAA4 21-122; SEQ ID NO: 14)
WRSFFKEALQGVGDMGRAYWDIMISNHQNSNRYLYARGNYDAAQRGPGG
VWAAKLISRSRVYLQGLIDCYLFGNSSTVLEDSKSNEKAEEWGRSGKDP
DRFR C-reactive protein
(19409 Da, CRP 10-185; SEQ ID NO: 15)
VFPKESDTSYVSLKAPLTKPLKAFTVCLHFYTELSSTRGYSIFSYATKR
QDNEILIFWSKDIGYSFTVGGSEILFEVPEVTVAPVHICTSWESASGIV
EFWVDGKPRVRKSLKKGYTVGAEASIILGQEQDSFGGNFEGSQSLVGDI
GNVNMWDFVLSPDEINTIYLGGPFSPNVL Apolipoprotein A1
(28077 Da, Apo A1 56-267; SEQ ID NO: 6)
DEPPQSPWDR VKDLATVYVDVLKDSGRDYVSQFEGSALGKQLNLKLLD
NWDSVTSTFSKLREQLGPVTQEFWDNLEKETEGLRQEMSKDLEEVKAKV
QPYLDDFQKKWQEEMELYRQKVEPLRAELQEGARQKLHELQEKLSPLGE
EMRDRARAHVDALRTHLAPYSDELRQRLAARLEALKENGGARLAEYHAK
ATEHLSTLSEKAKPALEDLRQGLLPVLESFKVSFLSALEEYTKKLNTQ Apolipoprotein E
(36747 Da, Apo 19-317, Glycosylated; SEQ ID NO: 16)
KVEQAVETEPEPELRQQTEWQSGQRWELALGRFWDYLRWVQTLSEQVQE
ELLSSQVTQELRALMDETMKELKAYKSELEEQLTPVAEETRARLSKELQ
AAQARLGADMEDVCGRLVQYRGEVQAMLGQSTEELRVRLASHLRKLRKR
LLRDADDLQKRLAVYQAGAREGAERGLSAIRERLGPLVEQGRVRAATVG
SLAGQPLQERAQAWGERLRARMEEMGSRTRDRLDEVKEQVAEVRAKLEE
QAQQIRLQAEAFQARLKSWFEPLVEDMQRQWAGLVEKVQAAVGTSAAPV
PSDNH Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A kit comprising:
   (a) a solid support coated with polyclonal or monoclonal antibodies, wherein the antibodies comprise antibodies specific to Apolipoprotein A1 (Apo A1), Complement C1 inhibitor (C1-inh), and Alpha-2-macroglobulin (A2M);
   (b) polyclonal or monoclonal antibody-substrate conjugates, wherein the substrate comprises a chromogenic or fluorescent reagent, and wherein the conjugates are reactive with the antibodies of (a); and
   (c) Apo A1, C1-inh, and A2M, as antigen standards.

2. The kit of claim 1, wherein the antibodies of (a) further include antibodies specific to Inter-alpha-trypsin inhibitor heavy chain H4 (ITIH4).

3. The kit of claim 1, wherein the antibodies of (a) further include antibodies specific to α-1 anti-chymotrypsin (AACT).

4. The kit of claim 1, wherein the antibodies of (a) further include antibodies specific to AACT and/or ITIH4 and/or Complement C4 Anaphylatoxin (C4A).

5. The kit of claim 1, wherein the solid support is a microtiter plate or membrane.

6. The kit of claim 1, wherein the solid support is a bead or particle.

7. The kit of claim 1, wherein the kit is an ELISA kit.

8. The kit of claim 1, wherein the solid support is a microbead array.

9. The kit of claim 1, wherein the antibodies of (a) are specific to 8 or fewer markers, and wherein the antibodies of (a) further comprise antibodies specific to up to five markers selected from the group consisting of: AACT, ITIH4, C4A, Serum Amyloid A (SAA), C-reactive Protein (CRP), Apolipoprotein E (ApoE), Alpha-1-antitrypsin (A1AT), ApoA1 fragment consisting of SEQ ID NO: 5, A1AT fragment consisting of SEQ ID NO: 11, and C4A (SEQ ID NO: 2 or 3).

10. The kit of claim 1, wherein the antibodies of (a) further comprise antibodies specific to AACT and ITIH4.

11. A method for assaying a combination of markers in a sample of biological fluid obtained from a human subject, the method comprising performing an immunoassay by contacting the sample with the solid support of the kit of claim 1.

12. The method of claim 11, wherein the immunoassay is an ELISA.

13. The method of claim 11, wherein the solid support is a microbead array.

14. The method of claim 11, wherein the sample is plasma or serum.

15. The method of claim 11, further comprising contacting the sample with the conjugates of the kit, and assaying the reaction of the conjugates with the sample.

16. The method of claim 15, further comprising contacting the antigen standards with the solid support and the conjugates, and assaying the relative levels of Apo A1, C1-inh, and A2M in the sample relative to the antigen standards.

17. A method of assaying Apolipoprotein A1 (Apo A1), Complement C1 inhibitor (C1-inh), and Alpha-2-macroglobulin (A2M) in a sample of serum or plasma, the method comprising contacting the sample with the solid support and the conjugates of the kit of claim 1; wherein the solid support comprises a microtiter plate, wherein the conjugates comprise alkaline phosphatase, wherein the chromogenic reagent comprises p-nitrophenyl-phosphate; and assaying the reaction of the conjugates with the sample.

18. The method of claim 17, further comprising assaying ITIH4.

19. The method of claim 17, further comprising assaying AACT and A1AT.

* * * * *

SEQUENCE LISTING

```
<160> NUMBER OF SEQ ID NOS: 18

<210> SEQ ID NO 1
<211> LENGTH: 77
<212> TYPE: PRT
<213> ORGANISM: Homo sapiens

<400> SEQUENCE: 1

Asn Val Asn Phe Gln Lys Ala Ile Asn Glu Lys Leu Gly Gln Tyr Ala
1               5                   10                  15

Ser Pro Thr Ala Lys Arg Cys Cys Gln Asp Gly Val Thr Arg Leu Pro
            20                  25                  30

Met Met Arg Ser Cys Glu Gln Arg Ala Ala Arg Val Gln Gln Pro Asp
        35                  40                  45
```

Cys Arg Glu Pro Phe Leu Ser Cys Cys Gln Phe Ala Glu Ser Leu Arg
            50                  55                  60

Lys Lys Ser Arg Asp Lys Gly Gln Ala Gly Leu Gln Arg
65                  70                  75

<210> SEQ ID NO 2
<211> LENGTH: 45
<212> TYPE: PRT
<213> ORGANISM: Homo sapiens

<400> SEQUENCE: 2

Cys Cys Gln Asp Gly Val Thr Arg Leu Pro Met Met Arg Ser Cys Glu
1               5                   10                  15

Gln Arg Ala Ala Arg Val Gln Gln Pro Asp Cys Arg Glu Pro Phe Leu
            20                  25                  30

Ser Cys Cys Gln Phe Ala Glu Ser Leu Arg Lys Lys Ser
            35                  40                  45

<210> SEQ ID NO 3
<211> LENGTH: 45
<212> TYPE: PRT
<213> ORGANISM: Homo sapiens

<400> SEQUENCE: 3

Thr Ala Lys Arg Cys Cys Gln Asp Gly Val Thr Arg Leu Pro Met Met
1               5                   10                  15

Arg Ser Cys Glu Gln Arg Ala Ala Arg Val Gln Gln Pro Asp Cys Arg
            20                  25                  30

Glu Pro Phe Leu Ser Cys Cys Gln Phe Ala Glu Ser Leu
            35                  40                  45

<210> SEQ ID NO 4
<211> LENGTH: 267
<212> TYPE: PRT
<213> ORGANISM: Homo sapiens

<400> SEQUENCE: 4

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
            50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
                100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
        130                 135                 140

Pro Leu Arg Ala Glu Leu Gln Glu Gly Ala Arg Gln Lys Leu His Glu
145                 150                 155                 160

```
Leu Gln Glu Lys Leu Ser Pro Leu Gly Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 5
<211> LENGTH: 36
<212> TYPE: PRT
<213> ORGANISM: Homo sapiens

<400> SEQUENCE: 5

Ala Glu Leu Gln Glu Gly Ala Arg Gln Lys Leu His Glu Leu Gln Glu
1               5                   10                  15

Lys Leu Ser Pro Leu Gly Glu Glu Met Arg Asp Arg Ala Arg Ala His
            20                  25                  30

Val Asp Ala Leu
        35

<210> SEQ ID NO 6
<211> LENGTH: 243
<212> TYPE: PRT
<213> ORGANISM: Homo sapiens

<400> SEQUENCE: 6

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175
```

```
Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 7
<211> LENGTH: 423
<212> TYPE: PRT
<213> ORGANISM: Homo sapiens

<400> SEQUENCE: 7

Met Glu Arg Met Leu Pro Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
    50                  55                  60

Val Leu Lys Ala Pro Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Gly Leu Lys Phe Asn Leu Thr Glu Thr Ser Glu
            100                 105                 110

Ala Glu Ile His Gln Ser Phe Gln His Leu Leu Arg Thr Leu Asn Gln
        115                 120                 125

Ser Ser Asp Glu Leu Gln Leu Ser Met Gly Asn Ala Met Phe Val Lys
    130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Leu Asp Ser Gln Thr Met Met Val Leu Val
        195                 200                 205

Asn Tyr Ile Phe Phe Lys Ala Lys Trp Glu Met Pro Phe Asp Pro Gln
    210                 215                 220

Asp Thr His Gln Ser Arg Phe Tyr Leu Ser Lys Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
            260                 265                 270

Ser Ala Leu Phe Ile Leu Pro Asp Gln Asp Lys Met Glu Glu Val Glu
        275                 280                 285

Ala Met Leu Leu Pro Glu Thr Leu Lys Arg Trp Arg Asp Ser Leu Glu
    290                 295                 300
```

```
Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
            325                 330                 335

Phe Thr Ser Lys Ala Asp Leu Ser Gly Ile Thr Gly Ala Arg Asn Leu
            340                 345                 350

Ala Val Ser Gln Val Val His Lys Ala Val Leu Asp Val Phe Glu Glu
            355                 360                 365

Gly Thr Glu Ala Ser Ala Thr Ala Val Lys Ile Thr Leu Leu Ser
            370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
            405                 410                 415

Val Thr Asn Pro Lys Gln Ala
            420
```

<210> SEQ ID NO 8
<211> LENGTH: 38
<212> TYPE: PRT
<213> ORGANISM: Homo sapiens

<400> SEQUENCE: 8

```
Ala Leu Val Glu Thr Arg Thr Ile Val Arg Phe Asn Arg Pro Phe Leu
1               5                   10                  15

Met Ile Ile Val Pro Thr Asp Thr Gln Asn Ile Phe Phe Met Ser Lys
            20                  25                  30

Val Thr Asn Pro Lys Gln
            35
```

<210> SEQ ID NO 9
<211> LENGTH: 433
<212> TYPE: PRT
<213> ORGANISM: Homo sapiens

<400> SEQUENCE: 9

```
Met Glu Arg Met Leu Pro Leu Leu Ala Leu Gly Leu Leu Ala Ala Gly
1               5                   10                  15

Phe Cys Pro Ala Val Leu Cys His Pro Asn Ser Pro Leu Asp Glu Glu
            20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
    50                  55                  60

Val Leu Lys Ala Leu Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
            85                  90                  95

Thr Glu Ile Leu Lys Ala Ser Ser Ser Pro His Gly Asp Leu Leu Arg
            100                 105                 110

Gln Lys Phe Thr Gln Ser Phe Gln His Leu Arg Ala Pro Ser Ile Ser
            115                 120                 125

Ser Ser Asp Glu Leu Gln Leu Ser Met Gly Asn Ala Met Phe Val Lys
    130                 135                 140

Glu Gln Leu Ser Leu Leu Asp Arg Phe Thr Glu Asp Ala Lys Arg Leu
145                 150                 155                 160
```

```
Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Pro Asp Ser Gln Thr Met Met Val Leu Val
            195                 200                 205

Asn Tyr Ile Phe Phe Lys Ala Lys Trp Glu Met Pro Phe Asp Pro Gln
        210                 215                 220

Asp Thr His Gln Ser Arg Phe Tyr Leu Ser Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Leu Lys Tyr Thr Gly Asn Ala
                260                 265                 270

Ser Ala Leu Phe Ile Leu Pro Asp Gln Asp Lys Met Glu Glu Val Glu
                275                 280                 285

Ala Met Leu Leu Pro Glu Thr Leu Lys Arg Trp Arg Asp Ser Leu Glu
        290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
                340                 345                 350

Ala Val Ser Gln Val Val His Lys Val Val Ser Asp Val Phe Glu Glu
                355                 360                 365

Gly Thr Glu Ala Ser Ala Ala Thr Ala Val Lys Ile Thr Leu Leu Ser
        370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Ser Lys Pro Arg Ala Cys Ile Lys Gln Trp Gly Ser
                420                 425                 430

Gln

<210> SEQ ID NO 10
<211> LENGTH: 418
<212> TYPE: PRT
<213> ORGANISM: Homo sapiens

<400> SEQUENCE: 10

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95
```

-continued

```
His Asp Glu Ile Leu Glu Gly Leu Asn Phe Asn Leu Thr Glu Ile Pro
                100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
195                 200                 205

Val Asn Tyr Ile Phe Phe Lys Gly Lys Trp Glu Arg Pro Phe Glu Val
210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys
```

<210> SEQ ID NO 11
<211> LENGTH: 22
<212> TYPE: PRT
<213> ORGANISM: Homo sapiens

<400> SEQUENCE: 11

```
Leu Met Ile Glu Gln Asn Thr Lys Ser Pro Leu Phe Met Gly Lys Val
1               5                   10                  15

Val Asn Pro Thr Gln Lys
            20
```

<210> SEQ ID NO 12
<211> LENGTH: 500

<212> TYPE: PRT
<213> ORGANISM: Homo sapiens

<400> SEQUENCE: 12

Met Ala Ser Arg Leu Thr Leu Leu Thr Leu Leu Leu Leu Leu Ala
1               5                   10                  15

Gly Asp Arg Ala Ser Ser Asn Pro Ala Thr Ser Ser Ser Ser Gln
            20                  25                  30

Asp Pro Glu Ser Leu Gln Asp Arg Gly Glu Gly Lys Val Ala Thr Thr
            35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
                100                 105                 110

Ser Pro Thr Gln Pro Thr Thr Gly Ser Phe Cys Pro Gly Pro Val Thr
            115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
                180                 185                 190

Leu Glu Ser Ile Leu Ser Tyr Pro Lys Asp Phe Thr Cys Val His Gln
            195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
    275                 280                 285

Leu Leu Asn Ala Ile Tyr Leu Ser Ala Lys Trp Lys Thr Thr Phe Asp
290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
    355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

```
Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ser Ala Ile Ser Val
450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500

<210> SEQ ID NO 13
<211> LENGTH: 36
<212> TYPE: PRT
<213> ORGANISM: Homo sapiens

<400> SEQUENCE: 13

Ala Arg Thr Leu Leu Val Phe Glu Val Gln Gln Pro Phe Leu Phe Val
1               5                   10                  15

Leu Trp Asp Gln Gln His Lys Phe Pro Val Phe Met Gly Arg Val Tyr
                20                  25                  30

Asp Pro Arg Ala
            35

<210> SEQ ID NO 14
<211> LENGTH: 102
<212> TYPE: PRT
<213> ORGANISM: Homo sapiens

<400> SEQUENCE: 14

Trp Arg Ser Phe Phe Lys Glu Ala Leu Gln Gly Val Gly Asp Met Gly
1               5                   10                  15

Arg Ala Tyr Trp Asp Ile Met Ile Ser Asn His Gln Asn Ser Asn Arg
                20                  25                  30

Tyr Leu Tyr Ala Arg Gly Asn Tyr Asp Ala Ala Gln Arg Gly Pro Gly
            35                  40                  45

Gly Val Trp Ala Ala Lys Leu Ile Ser Arg Ser Arg Val Tyr Leu Gln
        50                  55                  60

Gly Leu Ile Asp Cys Tyr Leu Phe Gly Asn Ser Ser Thr Val Leu Glu
65                  70                  75                  80

Asp Ser Lys Ser Asn Glu Lys Ala Glu Leu Trp Gly Arg Ser Gly Lys
                85                  90                  95

Asp Pro Asp Arg Phe Arg
            100

<210> SEQ ID NO 15
<211> LENGTH: 176
<212> TYPE: PRT
<213> ORGANISM: Homo sapiens

<400> SEQUENCE: 15

Val Phe Pro Lys Glu Ser Asp Thr Ser Tyr Val Ser Leu Lys Ala Pro
1               5                   10                  15
```

-continued

Leu Thr Lys Pro Leu Lys Ala Phe Thr Val Cys Leu His Phe Tyr Thr
             20                  25                  30

Glu Leu Ser Ser Thr Arg Gly Tyr Ser Ile Phe Ser Tyr Ala Thr Lys
         35                  40                  45

Arg Gln Asp Asn Glu Ile Leu Ile Phe Trp Ser Lys Asp Ile Gly Tyr
     50                  55                  60

Ser Phe Thr Val Gly Gly Ser Glu Ile Leu Phe Val Pro Glu Val
65                  70                  75                  80

Thr Val Ala Pro Val His Ile Cys Thr Ser Trp Glu Ser Ala Ser Gly
                 85                  90                  95

Ile Val Glu Phe Trp Val Asp Gly Lys Pro Arg Val Arg Lys Ser Leu
            100                 105                 110

Lys Lys Gly Tyr Thr Val Gly Ala Glu Ala Ser Ile Ile Leu Gly Gln
        115                 120                 125

Glu Gln Asp Ser Phe Gly Gly Asn Phe Glu Gly Ser Gln Ser Leu Val
    130                 135                 140

Gly Asp Ile Gly Asn Val Asn Met Trp Asp Phe Val Leu Ser Pro Asp
145                 150                 155                 160

Glu Ile Asn Thr Ile Tyr Leu Gly Gly Pro Phe Ser Pro Asn Val Leu
                165                 170                 175

<210> SEQ ID NO 16
<211> LENGTH: 299
<212> TYPE: PRT
<213> ORGANISM: Homo sapiens

<400> SEQUENCE: 16

Lys Val Glu Gln Ala Val Glu Thr Glu Pro Glu Pro Glu Leu Arg Gln
1               5                  10                  15

Gln Thr Glu Trp Gln Ser Gly Gln Arg Trp Glu Leu Ala Leu Gly Arg
             20                  25                  30

Phe Trp Asp Tyr Leu Arg Trp Val Gln Thr Leu Ser Glu Gln Val Gln
         35                  40                  45

Glu Glu Leu Leu Ser Ser Gln Val Thr Gln Glu Leu Arg Ala Leu Met
     50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                 85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

```
Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
            245                 250                 255

Phe Gln Ala Arg Leu Lys Ser Trp Phe Glu Pro Leu Val Glu Asp Met
        260                 265                 270

Gln Arg Gln Trp Ala Gly Leu Val Glu Lys Val Gln Ala Ala Val Gly
    275                 280                 285

Thr Ser Ala Ala Pro Val Pro Ser Asp Asn His
        290                 295

<210> SEQ ID NO 17
<211> LENGTH: 930
<212> TYPE: PRT
<213> ORGANISM: Homo sapiens

<400> SEQUENCE: 17

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Ile Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
        275                 280                 285

Lys Ile Gln Gln Thr Arg Glu Ala Leu Ile Lys Ile Leu Asp Asp Leu
```

-continued

```
                290                 295                 300
Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
                340                 345                 350

Asn Asp Ala Met Leu Met Ala Val Gln Leu Leu Asp Ser Ser Asn Gln
                355                 360                 365

Glu Glu Arg Leu Pro Glu Gly Ser Val Ser Leu Ile Ile Leu Leu Thr
                370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
                420                 425                 430

Asn Gly Gly Leu Ala Arg Arg Ile His Glu Asp Ser Asp Ser Ala Leu
                435                 440                 445

Gln Leu Gln Asp Phe Tyr Gln Glu Val Ala Asn Pro Leu Leu Thr Ala
                450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
                500                 505                 510

Leu Pro Thr Gln Asn Ile Thr Phe Gln Thr Glu Ser Ser Val Ala Glu
                515                 520                 525

Gln Glu Ala Glu Phe Gln Ser Pro Lys Tyr Ile Phe His Asn Phe Met
                530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
                580                 585                 590

Val Thr Lys Pro Asp Asp Gln Glu Gln Ser Gln Val Ala Glu Lys Pro
                595                 600                 605

Met Glu Gly Glu Ser Arg Asn Arg Asn Val His Ser Gly Ser Thr Phe
                610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
                660                 665                 670

Pro Gly Pro Pro Asp Val Pro Asp His Ala Ala Tyr His Pro Phe Arg
                675                 680                 685

Arg Leu Ala Ile Leu Pro Ala Ser Ala Pro Ala Thr Ser Asn Pro
                690                 695                 700

Asp Pro Ala Val Ser Arg Val Met Asn Met Lys Ile Glu Glu Thr Thr
705                 710                 715                 720
```

```
Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
    770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Leu Arg Asp Thr
    850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Glu Arg Arg Leu
            900                 905                 910

Asp Tyr Gln Glu Gly Pro Pro Gly Val Glu Ile Ser Cys Trp Ser Val
        915                 920                 925

Glu Leu
    930

<210> SEQ ID NO 18
<211> LENGTH: 1474
<212> TYPE: PRT
<213> ORGANISM: Homo sapiens

<400> SEQUENCE: 18

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
                20                  25                  30

Val Leu Val Pro Ser Leu Leu His Thr Glu Thr Thr Glu Lys Gly Cys
            35                  40                  45

Val Leu Leu Ser Tyr Leu Asn Glu Thr Val Thr Val Ser Ala Ser Leu
        50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
```

-continued

```
              145                 150                 155                 160
Leu Ile Pro Leu Val Tyr Ile Gln Asp Pro Lys Gly Asn Arg Ile Ala
              165                 170                 175
Gln Trp Gln Ser Phe Gln Leu Glu Gly Gly Leu Lys Gln Phe Ser Phe
              180                 185                 190
Pro Leu Ser Ser Glu Pro Phe Gln Gly Ser Tyr Lys Val Val Val Gln
              195                 200                 205
Lys Lys Ser Gly Gly Arg Thr Glu His Pro Phe Thr Val Glu Glu Phe
              210                 215                 220
Val Leu Pro Lys Phe Glu Val Gln Val Thr Val Pro Lys Ile Ile Thr
225                 230                 235                 240
Ile Leu Glu Glu Glu Met Asn Val Ser Val Cys Gly Leu Tyr Thr Tyr
                              245                 250                 255
Gly Lys Pro Val Pro Gly His Val Thr Val Ser Ile Cys Arg Lys Tyr
                        260                 265                 270
Ser Asp Ala Ser Asp Cys His Gly Glu Asp Ser Gln Ala Phe Cys Glu
                  275                 280                 285
Lys Phe Ser Gly Gln Leu Asn Ser His Gly Cys Phe Tyr Gln Gln Val
              290                 295                 300
Lys Thr Lys Val Phe Gln Leu Lys Arg Lys Glu Tyr Glu Met Lys Leu
305                 310                 315                 320
His Thr Glu Ala Gln Ile Gln Glu Glu Gly Thr Val Val Glu Leu Thr
                              325                 330                 335
Gly Arg Gln Ser Ser Glu Ile Thr Arg Thr Ile Thr Lys Leu Ser Phe
                        340                 345                 350
Val Lys Val Asp Ser His Phe Arg Gln Gly Ile Pro Phe Phe Gly Gln
                  355                 360                 365
Val Arg Leu Val Asp Gly Lys Gly Val Pro Ile Pro Asn Lys Val Ile
              370                 375                 380
Phe Ile Arg Gly Asn Glu Ala Asn Tyr Tyr Ser Asn Ala Thr Thr Asp
385                 390                 395                 400
Glu His Gly Leu Val Gln Phe Ser Ile Asn Thr Thr Asn Val Met Gly
                              405                 410                 415
Thr Ser Leu Thr Val Arg Val Asn Tyr Lys Asp Arg Ser Pro Cys Tyr
                        420                 425                 430
Gly Tyr Gln Trp Val Ser Glu Glu His Glu Glu Ala His His Thr Ala
                  435                 440                 445
Tyr Leu Val Phe Ser Pro Ser Lys Ser Phe Val His Leu Glu Pro Met
              450                 455                 460
Ser His Glu Leu Pro Cys Gly His Thr Gln Thr Val Gln Ala His Tyr
465                 470                 475                 480
Ile Leu Asn Gly Gly Thr Leu Leu Gly Leu Lys Lys Leu Ser Phe Tyr
                              485                 490                 495
Tyr Leu Ile Met Ala Lys Gly Gly Ile Val Arg Thr Gly Thr His Gly
                        500                 505                 510
Leu Leu Val Lys Gln Glu Asp Met Lys Gly His Phe Ser Ile Ser Ile
                  515                 520                 525
Pro Val Lys Ser Asp Ile Ala Pro Val Ala Arg Leu Leu Ile Tyr Ala
              530                 535                 540
Val Leu Pro Thr Gly Asp Val Ile Gly Asp Ser Ala Lys Tyr Asp Val
545                 550                 555                 560
Glu Asn Cys Leu Ala Asn Lys Val Asp Leu Ser Phe Ser Pro Ser Gln
                              565                 570                 575
```

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
            595                 600                 605

Pro Asp Ala Glu Leu Ser Ala Ser Ser Val Tyr Asn Leu Leu Pro Glu
610                 615                 620

Lys Asp Leu Thr Gly Phe Pro Gly Pro Leu Asn Asp Gln Asp Asn Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
            675                 680                 685

Cys Pro Gln Leu Gln Gln Tyr Glu Met His Gly Pro Glu Gly Leu Arg
            690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
            755                 760                 765

Ala Phe Cys Leu Ser Glu Asp Ala Gly Leu Gly Ile Ser Ser Thr Ala
            770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
            835                 840                 845

Cys Ala Asn Gly Arg Gln Thr Val Ser Trp Ala Val Thr Pro Lys Ser
850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Val Glu Glu Ser Ala
            930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

```
Thr Gln Gln Leu Thr Pro Glu Ile Lys Ser Lys Ala Ile Gly Tyr Leu
        995                 1000                1005

Asn Thr Gly Tyr Gln Arg Gln Leu Asn Tyr Lys His Tyr Asp Gly
        1010                1015                1020

Ser Tyr Ser Thr Phe Gly Glu Arg Tyr Gly Arg Asn Gln Gly Asn
        1025                1030                1035

Thr Trp Leu Thr Ala Phe Val Leu Lys Thr Phe Ala Gln Ala Arg
        1040                1045                1050

Ala Tyr Ile Phe Ile Asp Glu Ala His Ile Thr Gln Ala Leu Ile
        1055                1060                1065

Trp Leu Ser Gln Arg Gln Lys Asp Asn Gly Cys Phe Arg Ser Ser
        1070                1075                1080

Gly Ser Leu Leu Asn Asn Ala Ile Lys Gly Gly Val Glu Asp Glu
        1085                1090                1095

Val Thr Leu Ser Ala Tyr Ile Thr Ile Ala Leu Leu Glu Ile Pro
        1100                1105                1110

Leu Thr Val Thr His Pro Val Val Arg Asn Ala Leu Phe Cys Leu
        1115                1120                1125

Glu Ser Ala Trp Lys Thr Ala Gln Glu Gly Asp His Gly Ser His
        1130                1135                1140

Val Tyr Thr Lys Ala Leu Leu Ala Tyr Ala Phe Ala Leu Ala Gly
        1145                1150                1155

Asn Gln Asp Lys Arg Lys Glu Val Leu Lys Ser Leu Asn Glu Glu
        1160                1165                1170

Ala Val Lys Lys Asp Asn Ser Val His Trp Glu Arg Pro Gln Lys
        1175                1180                1185

Pro Lys Ala Pro Val Gly His Phe Tyr Glu Pro Gln Ala Pro Ser
        1190                1195                1200

Ala Glu Val Glu Met Thr Ser Tyr Val Leu Leu Ala Tyr Leu Thr
        1205                1210                1215

Ala Gln Pro Ala Pro Thr Ser Glu Asp Leu Thr Ser Ala Thr Asn
        1220                1225                1230

Ile Val Lys Trp Ile Thr Lys Gln Gln Asn Ala Gln Gly Gly Phe
        1235                1240                1245

Ser Ser Thr Gln Asp Thr Val Val Ala Leu His Ala Leu Ser Lys
        1250                1255                1260

Tyr Gly Ala Ala Thr Phe Thr Arg Thr Gly Lys Ala Ala Gln Val
        1265                1270                1275

Thr Ile Gln Ser Ser Gly Thr Phe Ser Ser Lys Phe Gln Val Asp
        1280                1285                1290

Asn Asn Asn Arg Leu Leu Leu Gln Gln Val Ser Leu Pro Glu Leu
        1295                1300                1305

Pro Gly Glu Tyr Ser Met Lys Val Thr Gly Glu Gly Cys Val Tyr
        1310                1315                1320

Leu Gln Thr Ser Leu Lys Tyr Asn Ile Leu Pro Glu Lys Glu Glu
        1325                1330                1335

Phe Pro Phe Ala Leu Gly Val Gln Thr Leu Pro Gln Thr Cys Asp
        1340                1345                1350

Glu Pro Lys Ala His Thr Ser Phe Gln Ile Ser Leu Ser Val Ser
        1355                1360                1365

Tyr Thr Gly Ser Arg Ser Ala Ser Asn Met Ala Ile Val Asp Val
        1370                1375                1380

Lys Met Val Ser Gly Phe Ile Pro Leu Lys Pro Thr Val Lys Met
```

```
                1385                1390                1395
Leu Glu Arg Ser Asn His Val Ser Arg Thr Glu Val Ser Ser Asn
        1400                1405                1410

His Val Leu Ile Tyr Leu Asp Lys Val Ser Asn Gln Thr Leu Ser
        1415                1420                1425

Leu Phe Phe Thr Val Leu Gln Asp Val Pro Val Arg Asp Leu Lys
        1430                1435                1440

Pro Ala Ile Val Lys Val Tyr Asp Tyr Tyr Glu Thr Asp Glu Phe
        1445                1450                1455

Ala Ile Ala Glu Tyr Asn Ala Pro Cys Ser Lys Asp Leu Gly Asn
        1460                1465                1470

Ala
```